(12) United States Patent
Morariu

(10) Patent No.: US 12,011,496 B2
(45) Date of Patent: Jun. 18, 2024

(54) TOPICAL MACQUI BERRY FORMULATION

(71) Applicant: Tracie Martyn International, Inc., New York, NY (US)

(72) Inventor: Marius Morariu, Brooklyn, NY (US)

(73) Assignee: Tracie Martyn International, Inc., New York, NY (US)

( * ) Notice: Subject to any disclaimer, the term of this patent is extended or adjusted under 35 U.S.C. 154(b) by 0 days.

(21) Appl. No.: 17/306,203

(22) Filed: May 3, 2021

(65) Prior Publication Data

US 2022/0105017 A1    Apr. 7, 2022

Related U.S. Application Data

(63) Continuation of application No. 16/252,267, filed on Jan. 18, 2019, now Pat. No. 10,993,897, which is a continuation of application No. 15/290,902, filed on Oct. 11, 2016, now abandoned, which is a continuation of application No. 14/480,182, filed on Sep. 8, 2014, now Pat. No. 9,463,153, which is a continuation of application No. 13/226,834, filed on Sep. 7, 2011, now Pat. No. 8,828,458, which is a continuation of application No. 11/525,288, filed on Sep. 21, 2006, now abandoned.

(60) Provisional application No. 60/719,530, filed on Sep. 21, 2005.

(51) Int. Cl.

| | | |
|---|---|---|
| *A61K 36/00* | (2006.01) |
| *A23L 2/52* | (2006.01) |
| *A61K 8/11* | (2006.01) |
| *A61K 8/14* | (2006.01) |
| *A61K 8/44* | (2006.01) |
| *A61K 8/46* | (2006.01) |
| *A61K 8/49* | (2006.01) |
| *A61K 8/60* | (2006.01) |
| *A61K 8/9789* | (2017.01) |
| *A61K 8/9794* | (2017.01) |
| *A61K 9/00* | (2006.01) |
| *A61K 9/127* | (2006.01) |
| *A61K 36/185* | (2006.01) |
| *A61K 45/06* | (2006.01) |
| *A61Q 1/00* | (2006.01) |
| *A61Q 1/02* | (2006.01) |
| *A61Q 19/00* | (2006.01) |
| *A61Q 19/08* | (2006.01) |
| *C11C 5/00* | (2006.01) |

(52) U.S. Cl.
CPC ................... *A61K 8/44* (2013.01); *A23L 2/52* (2013.01); *A61K 8/11* (2013.01); *A61K 8/14* (2013.01); *A61K 8/46* (2013.01); *A61K 8/4913* (2013.01); *A61K 8/602* (2013.01); *A61K 8/9789* (2017.08); *A61K 8/9794* (2017.08); *A61K 9/0053* (2013.01); *A61K 9/127* (2013.01); *A61K 36/185* (2013.01); *A61K 45/06* (2013.01); *A61Q 1/00* (2013.01); *A61Q 1/02* (2013.01); *A61Q 19/00* (2013.01); *A61Q 19/08* (2013.01); *C11C 5/002* (2013.01); *A23V 2002/00* (2013.01); *A61K 2800/26* (2013.01); *A61K 2800/43* (2013.01); *A61K 2800/52* (2013.01); *A61K 2800/522* (2013.01); *A61K 2800/524* (2013.01); *A61K 2800/56* (2013.01); *A61K 2800/74* (2013.01)

(58) Field of Classification Search
CPC ............. A61K 8/11; A61K 8/14; A61K 9/127
See application file for complete search history.

(56) References Cited

U.S. PATENT DOCUMENTS

| | | | |
|---|---|---|---|
| 3,869,554 A | 3/1975 | Pittet et al. | |
| 4,640,842 A | 2/1987 | May | |
| 5,011,855 A | 4/1991 | Traitler et al. | |
| 5,908,650 A | 6/1999 | Lenoble et al. | |
| 6,361,786 B1 | 3/2002 | Shanbrom | |
| 6,562,356 B2 | 5/2003 | Verite et al. | |
| 2002/0044913 A1 | 4/2002 | Hamilton | |
| 2002/0187114 A1* | 12/2002 | Mankovitz | A61K 8/602 424/769 |
| 2003/0118525 A1 | 6/2003 | Grigg | |
| 2003/0161897 A1 | 8/2003 | Shanbrom | |
| 2004/0022818 A1 | 2/2004 | Cho et al. | |
| 2004/0166069 A1 | 8/2004 | Gupta | |
| 2005/0013880 A1* | 1/2005 | Magnuson | A61K 31/353 424/732 |

(Continued)

FOREIGN PATENT DOCUMENTS

| | | |
|---|---|---|
| EP | 0834302 A1 | 4/1998 |
| JP | S63254181 A | 10/1988 |
| WO | 98/05294 A1 | 2/1998 |

OTHER PUBLICATIONS

Tsuda et al, Inhibition of lipid peroxidation and the active oxygen radical scavenging effect of anthocyanin pigments isolated from Phaseolus vulgaris L. Biochemical Pharmacology, (Oct. 11, 1996) vol. 52, No. 7, pp. 1033-1039 (Year: 1996).*

(Continued)

*Primary Examiner* — Qiuwen Mi
(74) *Attorney, Agent, or Firm* — Locke Lord LLP; Nicholas J. DiCeglie, Jr.

(57) ABSTRACT

The present invention provides a topical formulation and method of use where the formulation comprises *macqui* berry or a *macqui* berry extract containing anthocyanins having a very high oxygen radical absorbance capacity (ORAC). The formulation provides the *macqui* berry in a stabilized form which includes a glucuronide or glycuronide, a photostabilizing agent, encapsulation, or light- and/or air-blocking packaging.

18 Claims, No Drawings

(56) References Cited

U.S. PATENT DOCUMENTS

| | | | |
|---|---|---|---|
| 2005/0166336 A1* | 8/2005 | De La Mettrie | A61Q 5/00 8/405 |
| 2005/0244349 A1 | 11/2005 | Chaudhuri et al. | |
| 2006/0045896 A1 | 3/2006 | Morariu | |

OTHER PUBLICATIONS

Miranda-Rottmann et al , Juice and phenolic fractions of the berry *Aristotelia chilensis* inhibit LDL oxidation in vitro and protect human endothelial cells against oxidative stress. Journal of agricultural and food chemistry, 50 (26): 7542-7, 2002 (Year: 2002).*

Diaz et al, Spectrophotometric identification of anthocyanin pigments from "maqui" fruits (*Aristotelia chilensis,* Mol, Stuntz)Revista de Agroquimica y Tecnologia de Alimentos (1984), 24(4), 538-50. (Year: 1984).*

Miranda-Rottmann, Juice and phenolic fractions of the berry *Aristotelia chilensis* inhibit LDL oxidation in vitro and protect human endothelial cells against oxidative stress, Journal of Agricultural and Food Chemistry, 50 (26): 7542-7, (2002).

Liu et al., Microencapsulation of nurture edible anthocyanins, Shipin Gongye Keji 25 (12), 109-110, (2004).

Goihman-Yahr, Skin aging and photoaging: an outlook, Clinics in Dermatology 14: 153-160, (1996).

Soledad et al., Juice and phenolic fractions of the berry *Aristotelia chilensis* inhibit LDL oxidation in vitro and protect human endothelial ells against oxidative stress. Journal of agricultural and food chemistry. 50 (26): 7542-7547. (2002).

Diaz LS, et al., Spectrophotometric identification of anthocyanin pigments from Maqui fruits. (*Aristotelia Chilensis,* Mol. Stuntz), Rev Agroquim Tecnol Alimet 24 94), 538-550, (1984).

* cited by examiner

TOPICAL MACQUI BERRY FORMULATION

This Application is a Continuation of U.S. patent Ser. No. 16/252,267, filed on Jan. 18, 2019, now U.S. Pat. No. 10,993,897, which Application is a Continuation of U.S. patent application Ser. No. 15/290,902, filed on Oct. 11, 2016, which Application is a Continuation of U.S. patent application Ser. No. 14/480,182 filed on Sep. 8, 2014, now U.S. Pat. No. 9,463,153, which Application is a Continuation of U.S. patent application Ser. No. 13/226,834 filed on Sep. 7, 2011, now U.S. Pat. No. 8,828,458, which Application is a Continuation of U.S. patent application Ser. No. 11/525,288 filed on Sep. 21, 2006, which Application claims priority pursuant to 35 U.S.C. § 119 from U.S. Provisional Patent Application Ser. No. 60/719,530 filed Sep. 21, 2005, the disclosure of these applications are hereby incorporated by reference in their entirety.

FIELD OF THE INVENTION

The present invention relates to the topical application of compositions containing *macqui* berry or *macqui* berry extract in a topical formulation for the prevention and/or treatment of damage to skin, particularly skin damage resulting from chronoaging and photoaging.

BACKGROUND OF THE INVENTION

Skin is subject to abuse by many extrinsic (environmental) factors as well as intrinsic factors. A common extrinsic factor is exposure to ultraviolet radiation. Whether extrinsic or intrinsic, the abuse results in skin aging. Skin aging happens in two ways: (1) through the natural aging process which dermatologists call chronological aging (also known as chronoaging); and (2) through UV rays in sunlight accelerating the aging process which dermatologists call photoaging. Chronoaging results in thinning, loss of elasticity and general degradation of skin. As the skin naturally ages, there is a reduction in the cells and blood vessels that supply the skin. There is also a flattening of the dermal-epidermal junction which results in weaker mechanical resistance. As a consequence, older persons are more susceptible to blister formation in cues of mechanical traumas or disease processes (Oikarinen et al., Photodermatal. Photoimmunol. Photomed., 7:3-4 (1990)).

By contrast, photoaging, or premature aging, is a process in which the skin changes in appearance as a result of repeated exposure to sunlight. Typically, photoaging occurs in areas of habitual exposure, such as the scalp, face, ears, neck, chest, forearms and hands. The changes associated with photoaging include elastosis, atrophy, wrinkling, vascular changes (diffuse erythema, ecchymoses, and telangiectasias), pigmentary changes (lentigines, freckles, and areas of hypo- and hyper-pigmentation), and the development of seborrheic keratosis, actinic keratosis, corned ones and cysts.

Antioxidants are useful agents treating the skin from damage caused by chronoaging and photoaging. The most useful antioxidants are those that provide the highest capacity to absorb free radicals. The oxygen radical absorbance capacity (ORAC) is a measurement of this (Dreher F, Maibach H. Curr Probl Dermatol. 2001; 29:157-64.) Anthocyanins are a type of antioxidants that generally encompass a class of flavonoid compounds that are naturally occurring, water-soluble compounds, responsible for the red, purple, and blue colors of many fruits, vegetables, cereal grains, and flowers. Most anthocyanins have a high ORAC rating compared to other antioxidants and make them particularly useful for their topical antioxidative properties. Additionally, anthocyanins are collagenase inhibitors, which helps in the prevention and reduction of wrinkles, increase in skin elasticity, etc., which are caused by a reduction in skin collagen.

For ripe berries, a rich source of anthocyanin antioxidants, there is generally a linear relationship between ORAC values and anthocyanin content. High ORAC ratings are generally defined as greater than 25 μmole of Trolox equivalents (TE)/g. In most fruits, ORAC values ranged from 7.8 to 33.7 μmole TE/g of fresh berries and the ORAC values of the leaves range from 69.7 to 1822 μmole TE/g (Wang S Y, Lin H S., J Agric Food Chem. 2000 February; 48(2):140-6.). Comparatively, a fruit with an ORAC value of 8 μmol TE/g of fresh berries will have an ORAC value of about 35 μmol TE/g of dried berries and an ORAC of 34 μmol TE/g of fresh berries corresponds with an ORAC of 162 μcool TE/g dried matter. Black raspberries have a very high ORAC of 77 μmole TE/g while boysenberries have an ORAC of 48 μmole TE/g, and red raspberries and blueberries have an ORAC of 24 and 23 μmole TE/g, respectively. (http://www.deckerfarm.com/antioxidants.html). Acai is another fruit having a high ORAC content (167 ORAC units/g according to Brunswick Laboratories). Other fruit having high ORAC values include pomegranate (33.1 μμμmole TE/g) and *aronia* berry (62 μμmole TE/g) as well as whole coffee fruit extract (6250 ORAC units per gram according to Brunswick Laboratories). The stage at which the plant is harvested affects the ORAC value. Blackberries have their highest ORAC values during the green stages, whereas red raspberries have their highest ORAC values when ripe. The ORAC may be obtained by using the method described by the U.S. Department of Agriculture's Agricultural Research Service (Prior and Can, 83(4) J. AOAC INT. 950-6 (2000)). Additionally, testing for ORAC, H-ORAC, N-ORAC, S-ORAC, and ORAC-E (high throughput ORAC for oil-in-water emulsion) is available from Brunswick Laboratories (www.bruaswicldabs.com).

Anthocyanins have been formulated in topical form. For example, U.S. Pat. Pub. 2004/0022818 provides a skin care composition comprising fruit particles. Red and blue fruits, as well as other fruits which contain anthocyanins are included in this composition. Similarly, U.S. Pub. 2003/0161897 and U.S. Pat. No. 6,361,786 provide a topical antimicrobial factor having fruit juice (cranberry, *Aronia* berry, blackberry, grape or blueberry) and polyvinylprolidinone. A topical oil-in-water emulsion containing a surfactant/emulsifier and a lipid, which may be an anthocyanin-containing beery extract, is provided by WO 98/05294. U.S. Pat. No. 5,011,855 provides a cosmetic composition having a-linolenic acid and an oil extracted from *Ribes* genus fruits.

However, there are problems associated with these and other uses of antioxidants in a topical formulation. Particularly, antioxidants are readily oxidized and lose their antioxidant capacity. Additionally, some of the oxidation products of antioxidants will have a deleterious effect; for example, vitamin C oxidizes to dehydroascorbate which is known to lead to the formation of advanced glycation endproducts (AGEs) and therefore increase the signs of aging skin.

Therefore, a topical formulation containing an antioxidant with a much higher ORAC and consequently greater antioxidant power is needed in combination with a formulation that protects the antioxidant from degradation and loss of the anti-oxidative power to be used in treating and protecting the skin.

SUMMARY OF THE INVENTION

It is an object of the present invention to provide a composition and method for treating and protecting the skin.

In accordance therewith, a method and composition is provided for treating skin, comprising a topical composition containing *macqui* berry in a stabilized form and the administration of an effective amount of the topical composition to the skin.

In a preferred embodiment, the stabilized form of *macqui* berry includes a *macqui* berry or *macqui* berry extract and a glucuronide or glycuronide, or a dermatologically acceptable salt thereof.

In another embodiment, the stabilized form of *macqui* berry includes a *macqui* berry or *macqui* berry extract or a dermatologically acceptable salt thereof, which has been encapsulated or placed in light-blocking packaging.

Additional agents such as NADH, an antioxidant, an AGE inhibitor, a collagen enhancing agent, a mitochondrial resuscitant, a light reflecting agent or a sunscreen, an anti-edemic agent, a glutathione or an inducer thereof, an anti-inflammatory agent, a phenylpropanoid glycoside, a depigmenting agent or agent addressing hyperpigmentation, a skin-protective lipid, hyaluronic acid, an alpha hydroxy acid, an agent useful for treating hormonal decline, an anti-acne agent, an agent altering lipolytic activity, an anti-cellulite agent, an agent altering anti-capillary-fragility, an anti-elastase agent, an anti-erythema agent; or an agent that raises cyclic AMP may additionally be incorporated into the *macqui* berry composition.

In one embodiment, in addition to the administration of topical composition containing *macqui* berry in a stabilized form to the skin, *macqui* berry is also orally administered on its own or together with other antioxidants and synergistic compounds disclosed herein that are suitable for oral administration. This increases the protective effect on the skin.

In yet another embodiment of the present invention, the stabilized form of *macqui* berry is used in a cosmetic. Since the *macqui* berry formulation is a natural dye as well as an antioxidant, the formulation provides both color and antioxidation activity to the cosmetic.

Other features, advantages, and embodiments of the invention will be apparent to those skilled in the art from the following description and appended claims.

DETAILED DESCRIPTION

The present invention provides a formulation and method of use for treating skin and reducing the signs of aging. This formulation comprises *macqui* berry or an extract of *macqui* berry in a stabilized formulation.

I. Macqui Berry

*Macqui* berry (*Aristotelia Chilensis*) comes from a berry plant indigenous to Chile and Argentina. The anthocyanin content in the *macqui* berry is high. The juice has a total anthocyanin content of 203 mg anthocyanin per 100 ml juice. The ORAC of *macqui* berry 206 µmol TE/g (Cao, G, Prior, L. Agricultural Research, November 1996, p. 4-8 Brunswich Labs (2003)). This can be compared to other anthocyanin-containing fruit with high or moderately high ORAC values, as shown in Table 1.

TABLE 1

| Fruit | ORAC value (µµmole TE/g) |
|---|---|
| macqui berry | 206 |
| black raspberry | 77 |
| aronia berry | 62 |
| boysenberry | 48 |
| pomegranate | 33 |
| red raspberry | 24 |
| blueberry | 23 |

The *macqui* berry is particularly advantageous when used as a whole berry or partially purified extract. The berry or extract may be used as a liquid or juice, pulp, or in solid, dried form. Other compounds within the *macqui* berry are also advantageous for use in the topical formulation of the present invention *macqui* berry contains a number of anthocyanins including delphinidin-3-glucoarabinoside-5-glucoside; delphinidin 3,5-diglucoside-cyanidin-3-gluco arabino side-5-gluco side; cyanidin-3,5-diglucoside; delphinidin-3-glucoarabinoside; delphinidin-5-glucoarabinoside; delphinidin-3-gluco side; cyanidin-3-glucoarabinoside; and cyanidin-3-glucoside.

The *macqui* berry used in the present invention may also contain only the fruit or the fruit in combination with other parts of the plant, such as the leaves. Additional useful ingredients in the *macqui* include quercetin in the fruit and alkaloids in the leaves. These alkaloids are mostly indolic in nature and have anti-tumoral and antimicrobial activities; they include makonin, aristotelinone, aristoteline, aristotelone, aristotelinine, aristone, and others. Other agents found in the fruit include n-nonacosane, β-sitoesterol, antraquinone, and several triterpenes. The content of the *macqui* berry has been described by "Patagonal® Natural Antioxidants" BDS Nutraceuticals and DKSH Market Intelligence product brochure; Cesped, C. et al., Phytochemistry (1993) 34(3) 881-2; Cesped, C., et al, Phytochemistry, (1990) 29(4)1354-5; Munoz, O. et al, (2001) Medicinal plants in Chile: Chemistry and Pharmacognosis Editorial Universitaria University of Chile 330; and Miranda-Rottmnann. E., et al., (2002) L Agricul. Food Chem 50, 7542-7. However, these references do not provide a topical formulation that can be used for the prevention and/or treatment of damaged skin.

Quercetin, found in the fruit of the *macqui* berry, is a phenolic antioxidant. The pharmacological actions of phenolic antioxidants are primarily due to free radical scavenging and metal chelating properties. They also affect cell signaling pathways and gene expression. The ORAC activity order flavonol aglycones decreases in the order quercetin, myricetin and kaempferol (Soobrattee, M A, et al., Mutat Rea. 2005 Aug. 25). Quercetin has been used topically for the treatment of symptomatic diabetic peripheral neuropathy due to oxidative stress (Valensi P, J Diabetes Complications. 2005 Sep.-Oct.; 19(5):247-53.) Therefore, the presence of this ingredient in the berry is beneficial for the topical formulation.

Alkaloids, including makonin, aristotelinone, aristoteline, aristotelone, aristotelinine, aristone, have antimicrobial properties and therefore can be used in a topical preparation against acne vulgaris or to reduce the amount of preservatives needed in the topical formulation. Their anti-tumor effect may prove beneficial in preventing damage to skin from environmental tumor-inducing pollutants.

N-nonacosane is an anti-mutagenic. This is an important function in skincare as skin is exposed to pollutants and UV radiation on a daily basis that enhance the occurrence of mutation in the cells. Therefore, the combination of the anthocyanins and n-nonasosane in the formulation of the present invention are particularly advantageous in a topical formulation.

β-sitosterol is anti-inflammatory (Lawrence Review of Natural Products, 1995) anti-bacterial (Internat. J. Crude Drug Res. 28(1,2,3,4): 1990, page 155), anti-androgenic (Malin, T. and Vanithakumari, G. 1989, Journal of Ethnopharmacology, 28: 221-234, 1990), and an antioxidant, making it a valuable ingredient far topical formulations for akin damage from aging, acne or rosacea.

Antraquinone, and it derivatives are known to have antibacterial properties. (Chen C H, Yao Xue Xue Bao 1964; 11(4):258-65). Therefore, the combination of this agent with the anthocyanins is particularly advantageous due to the disinfectant properties of the formulation.

Therefore, the interactions between the different constituents of the *macqui* berry make it a novel, potent ingredient for topical application to address skin aging.

The *macqui* berry may be used as a whole fruit, a fruit juice, or an extract of the fruit with the optional addition of extract from the leaves or stem of the plant. The extract may be used in a liquid or solid form.

II. Stabilizer

Since *macqui* berry contains antioxidants having a high ORAC ratio, it is relatively unstable over time, especially when exposed to light and/or air. Therefore, the present invention provides a formulation where the antioxidant from the *macqui* berry is stabilized. Stabilizing agents include, for example, glucuronide, glucuronide, microencapsulation, and light- and/or air-blocking packaging. Other stabilizing agents such as diethylhexyl syringylidene malonate may be used. In one embodiment of the present invention, two or more different stabilizers are be used.

Flavonoid Glucuronides and Glycuronides

Flavonoid glucuronides and flavonoid glycuronides are added to the formulation of the current invention as a stabilizer for the *macqui* berry. As used herein, the term "flavonoid glucuronide" encompasses flavonoids that are attached to a glucuronic acid (e.g., glucose having a carboxylic acid at the C6 position on the sugar ring); the term also encompasses flavonoid glucosides, which are flavonoids attached to glucose. Similarly, flavonoid glycuronides are flavonoids attached to glycuronic acid, and flavonoid glycosides, which are herein encompassed in the term flavonoid glycuronides, are flavonoids attached to a glycose.

Exemplary flavonoid glucuronides include: luteolin 7-glucuronide; luteolin 3'-glucuronide; luteolin 7-diglucuronide; luteolin 7-glucuronide-3'-ferulyglucoside; apigenin 7-glucuronide; quercetin 3-(isoferulylglucuronide); 7-sulfatoglucuronides of tricin and luteolin; 3-glucuronide-7-sulfate of kaempferol, quercetin, or isorhamnetin; quercetin 3-glucuronide-3'-sulfate; gossypetin 8-glucuronide-3-sulfate; rhamnetin 3'-glucuronide-3,5,4'-trisulfate; the 7-glucuronide and 8-glucuronide of 5,7,8-trihydroxyflavone (norwogonin), 5,7,2' trihydroxyflavone 7-glucuronide; apigenin 7-rhamnosyl-(1->2)-galacturonide; apigenin 7-digalacturnide; apigenin 7-galacturonyl glucoside; apigenin 7-sulfatoglucuronide; 5,6,7,2'-tetrahydroxyflavone 7-glucuronide; 5,7,2'-trihydroxy-8-methoxyflavone 7-glucuronide; 5,7-dihydroxy-8,2'-dimethoxyflavone 7-glucuronide; luteolin 7-galacturonide-4'-glucoside; 8-hydroxyluteolin 4'-methyl ether 8-glucuronide; tricetin 7,3'-diglucuronide; tricetin 3'-methyl ether 7,5'-diglucuronide; apometzgerin 7-glucuronide; 8 hydroxytricetin 7-glucuronide; kaempferol 3-rhamnoside-7-galacturonide; kaempferol 3-glucoside-7-glucuronide; eupafolin 3-glucuronide; herbacetin 3-glucuronide-8-glucoside; quercetin 3-glucoside-7-glucuronide; quercetin 3-gentiobioside-7-glucuronide; quercetin 3-glucuronide-3'-sulfate; tamarixetin 5-glucoside-7-glucuronide; quercetin 3',4'-dimethyl ether 5-glucoside-7-glucuronide; gossypetin 3-glucoside 8-glucuronide; and gossypetin 3-glucuronide-8-glucoside.

Exemplary flavonoid glycuronides include 7-glycuronide luteolin and 7-glycuronide apigenin.

A particularly useful flavonoid glucuronide is the glucuronide derived from rosemary. Rosmarinic acid is a naturally-occurring flavonoid isolated from various plants, such as Rosmarinus officinalis (Ricerca Sci. 1958, 28, 2329), *Melissa officinalis* (Arch. Pharm. 1960, 293, 1043), and *Teucrium scorodonia* (Planta Med. 1965, 13: 3, 331). Rosmarinic acid may be obtained from these and other plants by extraction, (see U.S. Pat. No. 5,908,650), and also may be obtained from plant cell cultures, such as *Coleus blumei* (see Naturwissenschaften 1977, 64:11, 585; See also Liu, G., et al., Biochem Pharmacol., 1992 43, 147-152.)

Flavonoid glucuronides and glycuronides have been found to be useful in stabilizing, (e.g., reducing the rate of loss of anthocyanin color, intensity, and aromaticity, due to pH, heat, and/or light) anthocyanin-containing foods and beverages. See U.S. Pat. No. 5,908,650. As well as protecting the color of the anthocyanin and creating a color shift, flavonoid glucuronides and glycuronides can increase the stability of the *macqui* berry topical formulation, and allow for increased antioxidant activity both in the initial formulation of the topical composition and over time. This is particularly useful for topical formulations where the compound will likely sit on a shelf for a period of time before use in a water-based gel, serum, or oil-in-water emulsion.

Many of these glucuronides, such as rosmarinic acid, have antioxidant properties as well as stabilization properties. Therefore, the use of these glucuronides is advantageous in the present invention because of the additional antioxidative effective on the skin and underlying tissue of the composition. Rosmarinic acid has an $IC_{50}$ of 0.74 μM.

The flavonoid glucuronide or glycuronide is incorporated in the present composition in an amount effective to protect and stabilize the anthocyanin. This amount will depend on the amount and type of anthocyanin in the formulation; therefore, the ratio of flavonoid glucuronide or glycuronide to the *macqui* berry anthocyanins will vary to achieve effective stabilization of the anthocyanins. It is contemplated that the weight of flavonoid glucuronide used will be between 0.1% and 500% of the weight of anthocyanin used in the formulation. Preferably, the weight of flavonoid glucuronide or glycuronide is between about 0.2%-10% of the weight of anthocyanins. In a more preferred embodiment, the weight of flavonoid glucuronide or glycuronide is between about 0.5%-5% of the weight of anthocyanins.

In one embodiment of the present invention, the stabilizer is a stabilizer such as those described in U.S. Pat. Pub. 2005/0244349, herein incorporated by reference. These compounds are taught to be useful for stabilizing photosensitive poly-unsaturated and/or aromatic compound such as antioxidants against degradation from sun light, heat and air oxidation. The stabilizers include dialkylbenzalmalonates, monoalkyl-monoacyl benzalmalonate, dialkyl benzalmalonamide and monoalkyl-monoacyl benzalmalonamide compounds, and are able to stabilize photo-sensitive ingredients within the *macqui* berry formulation of the present invention. In particular, a preferred stabilizer is diethylhexyl syringylidene malonate.

Encapsulation

In one aspect of the present invention, the *macqui* berry formulation is stabilized using encapsulation, or more preferably, microencapsulation. Microencapsulation can protect the anthocyanin from the oxidative effects of the surrounding environment and increase the effectiveness as an anti-aging agent Processes conventionally used for microencapsulation may be employed, and may comprise encapsulation by nanosomes, liposomes, or other vehicles known in the art.

The microcapsules may be prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nano-particles and nanocapsules) or in macroemulsions. (Remington's Pharmaceutical Sciences, A. Osol ed., 16th ed. (1980)). Microencapsulation is particularly useful for formulations containing DHLA, which is prone to degradation and oxidation. In one preferred embodiment, the microencapsulating agent is biodegradable, such as a carbohydrate, a naturally occurring polymer, or lecithin.

One typical process is to dissolve the shell material in a solvent (in the form of a colloidal or true solution) and to disperse the core material in the resulting solution in the form of solids or micro-droplets. This dispersion is divided into micro-droplets and then heated using, for example, hot air. During this process, the solvent evaporates and the shell material re-precipitates in the form of solids and forms a shell around the core material. This gives cede microcapsules, which can then be subjected to the customary processing steps and incorporated into the final formulations. This process utilizes the known phenomenon of coacervation.

Another process of microencapsulation uses interface polymerization to create the microcapsule shell. In this method, precursors of the shell material, for example monomers, are concentrated onto the core material, where they polymerize to give the final shell film. Fat-coating processes also may be used.

The materials used for microencapsulation are selected from conventional hydrophilic or hydrophobic substances or mixtures thereof. Solids, in particular natural polymers, for example, starch and other polysaccharides, are preferred. However, synthetic polymers can also be used. Examples of shell materials are fats and/or waxes, preferably those having a solidification temperature of approximately 35°–80° C. and include mixtures of cetyl palmitate and cetyl alcohol. Other compounds include polysaccharides and their derivatives of natural or partially synthetic origin, (e.g. cellulose derivatives); further, polymers of α- and/or β-hydroxycarboxylic acids, in particular polymers of glycolic acid (polyglycolides), lactic acid (polylactides), α-hydroxybutyric acid (polyhydroxybutyrate), α-hydroxyvaleric acid (polyhydroxyvalerate) and/or their copolymers, or mixtures of such polymers and/or copolymers.

Independently of the specific technique for preparing the microcapsules, it is preferred to carry out the process at a temperature which does not cause any of the components of the formulation to decompose or lose their antioxidant activity.

Similarly, nanoencapsulation may be used. Nanoemulsions are meta-stable oil-in-water emulsions having a globule sin is less than 150 nm. They can be stabilized with amphiphilic lipids. Nanoemulsions are structurally distinct from microemulsions which are thermodynamically stable dispersions comprising micelles of at least one amphiphilic lipid swollen with oil and do not require mechanical energy to be prepared. An advantage of using nanoencapsulation is the reduced need for surfactants, which may tend to lead to intolerance and entailing a sticky feel when applied to the skin (see 6,562,356).

In one embodiment, the formulation is encapsulated in cyclodextrin. Such process is performed, for instance, by Wacker Fine Chemicals (www.wacker.com).

In another embodiment, the *macqui* berry formulation is encapsulated with NADH, R-DHLA, ATP, Glutathione, and SOD in Nano Spheres. Such process is performed, for instance, by Salvona Technologies. In another embodiment, biopolymer nanoemulsions from Ivrea-Pak Tech are used to eliminate undesirable residue ("ghosting") commonly associated with porous particulate entrapment formulations.

Packaging Materiel

The *macqui* berry formulation may be stabilized by placing the formulation in a packaging that blocks the radiation that causes oxidation of the berry components. Preferably, this package will block light from 450-750 nm, the visible range, which is known to damage most nutrients. The packaging material will preferably have less than 1% transmittance, or more particularly less than 0.1% transmittance within the range from 450-750 nm. The packaging should not contain polyvinyl chloride-containing polymers that degrade organic molecules to carcinogenic compounds. Dark violet packaging plastic or glass may be used in a particular embodiment. (mironglass.com.) The packaging may be additionally air-less and therefore prevent air from getting in contact with the formulation once opened. Additionally the packaging may be nitrogen-flushed to further protect the formulation.

III. Additional Agents

In addition to the *macqui* berry, the topical formulation in many preferred embodiments of this invention contains at least one or more additional active ingredients. A non-limiting list of such ingredients is included herein.

Collagen or Elastin Enhancing Agents

The collagen or elastin enhancing agent may be administered by applying the agent to the skin. Collagen enhancing agents such as those described herein may also be added to the present formulation. This increased collagen synthesis is an important aspect of the present invention, as it provides additional benefit to the skin and reduces the effects of aging. Agents having 'collagenic activities' include the anthocyanidins, ascorbic acid, *asiatic* acid (such as from *centella asiatica*), aucubin, proanthocyanidins, stabilized vitamin C, the amino acids 1-lysine, 1-proline and their derivatives (e.g., dipalmitoyl-hydroxy-proline, hydroxyproline, homoproline, and natural raw materials containing these such as apt (Ahnfeltia *concinna*) available from CIR)), and copper peptides. Agents having 'collagenase-inhibitor activities' include the anthocyanidins, eicosapentaenoic acid, proanthocyanidins such as grape seed proanthocyanins, procyanidins, bovine cartilage extracts, and glycosaminoglycans from shark. Agents having 'collagen-sparing activities' include caffeic acid, chlorogenic acid, cichoric acid, cynarin, and echinacoside. Each of these may be used in addition to the ATP enhancement of the present invention. Alternatively, collagen itself may be added to the formulation, such as in the form of collagen peptides (e.g. active collagen polypeptide available from Shanghai UChem Co. LTD.) or in a form adapted for delivery to the skin so that the collagen will penetrate into the skin (e.g., the form described in U.S. Pat. No. 6,759,056).

Other collagen inducing agents are growth factors, such as EGF, FGF, TGF, TGF-β, HGH, NGF, KGF, IGF, HGF natural sources containing growth factors such as colostrums (Pepha® Nutria from Centerchem), doer antler preparations and peptides designed to increase the production of any of these growth factors (e.g., Syn®-col from Centerchem-TGF-β, *Hericium* Erinaceus and Idebenone-NGF), or the production of collagen itself (e.g., Matrixyl300, Dermaxyl, and Calmosensine each from Sederma), collagen peptides and synthetic collagen inducing peptides (e.g., pal-kttks). Collagen stimulating agents are those such as TGF-beta, retinoic acid and retinol derivatives, botanical and other natural extracts such as *Vigna Aconitifolia* seed extracts, g-ascorbate and g-hel.

Glucosamine, glucoseamine sulfate, glucosamine HCl, glucosamine ascorbate, chondroitin sulfate and other glucosamine salts and derivatives may be used in the formulation to induce collagen. Manganese gluconate, a common source of manganese, may also be included in the formulation. The enzyme MnSOD, a powerful antioxidant that removes superoxide radicals, may also be used.

In one embodiment, carnosine is added to the formulation to stimulate collagen formation. Carnosine is degraded by histidine and carnosinase to form histamine and β-alanine and thereby stimulates the biosynthesis of nucleic acids and collagen (Nagai, K et al., Surgery 1986;100(5); 815-821). Carnosine is able to react with carbonyl groups on glycated or oxidized proteins (i.e., camosinylation) and inhibit the glycoxidised proteins from cross-linking with normal macromolecules and causing the signs of aging (Hipkiss A R, et al., Mech Ageing Dev 2001 Sep. 15; 122(13):1431-45; Hobart et al. Life Sci. 75:1379-89). In one embodiment, a silicon, or an ortho silica acid described in U.S. Pat. No. 5,922,360, may be used. This ingredient may be used to boost collagen production.

Carnosine, the dipeptide β-alanyl-L-histidine, and its related compounds such as anserine (11-alanyl-1-methyl-L-histidine) and homocarnosine (γ-amino-butyryl-L-histidine) as well as the closely related compound carcinine(β-alanyl-histamine) are preferred antioxidants exhibiting strong and specific antioxidant properties that may be added to the formulation of the present invention. Carnosine is present in millimolar concentrations in tissues, including skeletal muscle and brain, and is an anti-glycation agent and a free radical scavenger as well as an antioxidant. Useful carnosine include the dipeptide β-alanyl-L-histidine, D,L-carnosine, D-carnosine, L-carnosine, the derivatives anserine and homocarnosine, as well as their salts, such as zinc carnosine, copper camosine, and copper anserine (Hipkiss A R, Charm H, Biochem Biophys Res Commun. 248(1):28-32, 1998; Hipkiss A R et al., Ann N Y Acad Sci, 854:37-53, 1998).

When carnosine is chelated to zinc or copper ions, the presence of the ions enhances carnosine activity as a superoxide radical scavenger (Gulyaeva N.Y., Biochemistry 57 (7:2)1051-4, 1987). Therefore, the addition of carnosine as an agent in the present invention in chelated form provides for superoxide scavenger activity as well as the anti-glycation and anti-oxidation properties of carnosine. Carnosine has been administered at dosages above 500 mg/kg body weight in animal studies and has been found to be safe at these levels.

Anti-Glycation Agents

Anti-glycation agents may be used in the present invention both to protect the ATP enhancing agent and for the anti-glycation affect that decreases the signs of aging in the skin. The anti-glycation agent will protect the ATP enhancing agent by removing free radicals that would inactivate the ATP enhancing agent or counteract the glycation effect of the ATP enhancing agent.

As used herein, the term "anti-glycation agent" mans a compound useful for preventing and/or reducing the glycation of skin proteins, in particular of dermal proteins such as collagen. The anti-glycation agent inhibits the formation of advanced glycation end products (AGEs) and is also known as an AGE inhibitor.

Examples of anti-glycation agents are plant extracts of the Ericaceae family, such as an extract of blueberry (*Vaccinium angustifolium*), ergothioneine and its derivatives; and hydroxystilbenes and their derivatives, such as resveratrol and 3,3',5,5'-tetra-hydroxystilbene. Other exemplary inhibitors of AGE formation include, but are not limited to, benfotiamine, pyridoxamine, G-rutin (Nagasawa T., Mol Cell Biochem. 249(1-2):3-10, 2003); pyridoxal phosphate, aminoguanidine, a aminoguanidine-pyridoxal adduct, green tea (Ouyang P. Di Yi Jun Yi Da Xue Xue Bao 24(3): 247-51, 2004); extracts of *Thymus vulgaris* (Morimitsu et al., Biosci Biotechnol Biochem 59(11):2018-21, 1995); Ge-132(2-carboxyethyl germanium sequioxide) (Unakar et al., Exp. Eye Rea. 61(2): 155-64, 1995); curcumine (Sajithlal et al., Biochem Pharmacol. 56(12):1607-14, 1998); extracts of Cratoxylum cochinchinense (Tang, S Y et al., Free Radic. Biol. Med. 36(12):1575-87, 2004); extracts of *Apocynum venetum* Luobuma (Yokozawa et al., Food Chem. Toxicol. 42(6):975-81, 2004); carnosine; carnosinylated proteins (Hipkiss A R et al., Cell Mol Life Sci. 57(5):747-53, 2000); extracts of Eugenia bicyclis (Okada et al., Nat Prod. 67(1): 103-5, 2004); rutin (Kiho, T et al., Biosci. Biotechnol. Biochem. 68(1):200-5, 2004); amadoriase enzymes from *Aspergillus* fungi (Moonier V M et al., Biochem. Soc. Trans 31:1349-53, 2003; U.S. Pat. No. 6,605,642); guanidine rich extracts of *Galega officinalis*; and extracts of *lycoperrsicon esculentum*. The AGE inhibitor as described herein may be incorporated in amounts from about 0.001%-30% by weight. More preferably, the AGE inhibitor is incorporated in amounts from about 0.1%-5% by weight, based of the total weight of the preparation.

One preferred anti-glycation agent is carnosine. Carnosine, discussed above for its collagen enhancing properties, is also useful as an anti-glycation agent. Carnosine also promotes wound healing (Roberts P R, et al., Nutrition 1998; 14; 266-9), protects against radiation damage, is potentially a modulator of enzymatic activities, and has been shown to be a chelator of heavy metals (Quinn, P J et al., Mol. Aspects Med. 1992; 13(5), 379-444; (Hipkiss A R. Int J Biochem Cell Biol 1998; 30:863-8). Carnosine reacts strongly with aldehyde and keto groups of sugars by Amadori reaction, and is also theorized to deplete certain glycolysis intermediates. Therefore, a reduction of glycolysis intermediates by carnosine depletes their energy supply. But the addition of pyruvate reverses this effect. (Holliday R Br 3 Cancer. 1996 April; 73(8):966-7 1). Therefore, it is preferable to add camosine in a formulation with an agent which also reduces the amount of pyruvate available. Additionally, the reaction between carnosine and aldehydes protects susceptible macromolecules. Therefore, carnosine inhibits nonenzymic glycosylation and cross-linking of proteins induced by reactive aldehydes (aldose and ketone sugars, certain triose glycolytic intermediates and malondialdehyde (MDA), a lipid peroxidation product). (Hipkiss A R, et al., Ann N Y Mad Sci. 1998 Nov. 20; 854:37-53).

An anti-glycation agent of interest is garcinol. Garcinol occurs naturally in the latex exudate of the herb *Garcinia* Cambogia, which is used as a weight loss supplement. Garcinol is a moderate antioxidant, metal chelator, and free radical scavenger. It also is a superoxide anion scavenger and has been shown to suppress glycation in a bovine serum albumin/fructose system. (Yamaguchi F. et al., J Agric Food Chem. 2000 February; 48(2): 180-5). It has also been shown that the (−)-hydroxycitrate from *Garcinia* fruits may aid endurance during post-absorptive aerobic exercise by promoting gluconeogenesis. *Garcinia* is particularly useful as an additional agent because the combination of garcinol with carnitine and chromium will have anti-glycation properties and promote gluconeogenesis (McCarty M F. Med Hypotheses. 1995 September; 45(3):247-54).

Aglycal LS 8777, made by Laboratoires Serobiologique (Cognis France), may also be included as an anti-glycation agent in the formulation of the present invention. Aglycal LS 8777 is a plant-based complex that retards the glycation of proteins. This photo-complex aids in the long-term elasticity of the skin and protects against the fragmentation of collagen (www.laboratoires-serobiologiques.com)

Aldenine, made by Lipotec (Spain), is a complex of a tripeptide and hydrolyzed wheat and soy proteins that boosts Collagen III synthesis while protecting cells from photo damage. Aldenine detoxifies the skin from harmful RCS (Reactive Carbonyl Species).

Another anti-glycation agent, ANTIGLYSKIN® from Silab, is rich in phenolic acids and glycopeptides from sunflower and inhibits the protein glycation reaction and prevents the glyco-oxidation.

Compounds obtained from *Pterocarpus marsupium* may also be incorporated into the topical formulation. (−) Epi-catechin, the active ingredient in the Indian herb *Pterocarpus marsupium* Roxb, can be obtained from the water extract of the bark and is insulinogenic. (Ahmad F, et al., Acta Diabetol Lat. 1989 Oct.-Dec.; 26(4):291-300). It has been found to decrease hepatic and skeletal muscle glycogen (Grover J K, et al., Mol Cell Biochem. 2002 December; 241(1-2):53-9). In addition, three flavonoid antioxidants are also present in the heartwood; these flavonoid are marsupsin, pterosupin, and liquiritigenin. The gum tannic acid and a non-glucosidal tannin, kind tannic acid, and *Pterocarpus marsupium* extracts have also been shown to have anti-oxidant activity (Katiyar S K, et al., Photochem Photobiol. 1995 November; 62(5):855-61) and a strong anti-glycation agent (www.laboratoires-serobiologiques.com/LSvi/english/prod.sub.--2.html)).

N-Acetylcysteine is an N-acetylated cysteine which is a thiol containing amino acid, also called α-acetamido-β-mercaptopropanoic acid, which is a preferred additional component of the present invention. The incorporation of N-acetylcysteine into the topical formulation will improve the signs of aging of the skin. N-acetylcysteine is an antioxidant and also has been indicated as protective against pulmonary oxygen toxicity (Eur. Respir. J. 2: 116-126 (1989)). It is also an anti-glycation agent. Preferred forms of N-acetyl cysteine include: N-acetyl-L-cysteine, N-acetyl-L-cysteine amide, N-acetyl-L-cysteine methyl ester, N-acetyl-L-cysteine ethyl ester, N-acetyl-L-cysteine propyl ester, and N-acetyl-L-cysteine isopropyl ester. See PCT US96/16534 which teaches topical compositions containing N-acetylcysteine, and U.S. Pat. Pub. 2003/0229141 which discloses the topical use of N-acetyl cysteine to alleviate or improve various cosmetic conditions and dermatological disorders.

One preferred AGE inhibitor is benfotiamine and benfotiamine derivatives such as S-Benzoylthiamine O-monophosphate. Benfotiamine is the most potent of the allithiamines, a unique class of thiamine-derived compounds present in trace quantities in roasted crushed garlic and other vegetables from the *Allium* genus (such as onions, shallots, and leeks). Benfotiamine's unique open-ringed structure makes it able to pass directly through cell membranes, readily crossing the intestinal wall and being taken straight into the cell, and is absorbed by the body better than thiamine itself, and levels of thiamine and thiamine pyrophosphate remain higher for longer, thereby decreasing the formation of AGEs.

Another preferred anti-glycation agent is pyridoxamine. Pyridoxamine (4-aminomethyl-5-hydroxy-6-methyl-3-pyridinemethanol), and derivatives of pyridoxamine such as 4-aminomethyl-5-hydroxy-6-methyl-3-pyridinemethanol dihydrochloride and 4-aminomethyl-5-hydroxy-6-methyl-3-pyridylmethyl phosphate, may be incorporated in the ATP enhancing formulation of the present invention. Pyridoxamine is a vitamin B6 derivative which is water-soluble and nontoxic in rats and humans. It inhibits the formation of AGEs from Amadori proteins and is classified as a poet-Amadori inhibitor (Khalifah et al. Biochem. Biophys. Res. Comm. 199:257, p. 251-258). It is also believed that pyridoxamine traps reactive dicarbonyl intermediates in AGE formation and may also decrease oxidative stress, which subsequently decreases AGE formation from reactive oxygen species (Iacovella et al. SCJMM, 2004: 5, p. 73-101). Pyridoxamine has also been shown to inhibit advanced lipoxidation end products (ALES) (Onorato J M. et al., J. Biol. Chem. 275(28):21177-84 (2000)). Decreasing ALEs formation is accomplished by decreasing the concentration of an oxidiable substrate such as glucose and blood lipids (Metz T O, et al., Arch Biochem Biophys. 419(1):41-9 (2003)). It has been proposed that the antioxidant properties of pyridoxamine be used for the inhibition of ALE as well as AGE formation and development of complications of diabetes and hyperlipidemia (Mene P, et al, Am J Cardiovasc Drugs. 3(5):315-20 (2003)). U.S. Pat. Nos. 6,750,209 and 6,740,668 demonstrate the difference in pyridoxamine and the other 136 vitamins as inhibitors of post-Amadori antigenic AGE formation. The efficacy of inhibition of overall glycation of protein, in the presence of high concentrations of sugar, was not predictive of the ability to inhibit the post-Amadori steps of AGE formation where free sugar is removed. Pyridoxamine has been shown to be the strongest AGE inhibitor of the B vitamins. (Price, D. L., J. Biol. Chem. 2001 Dec. 28; 276(52):48967-72).

The combination of benfotiamine and pyridoxamine for AGE inhibition is also a preferred additional ingredient that may be added to the formulation of the present invention. This combination is discussed in U.S. Pat. Pub. 2006/0045896-A1, herein incorporated by reference AGE inhibitors that may be added to the formulation include the enzymes, fructosyl lysine oxidase and fructose lysine 3-phosphokinase, which catalyze the deglycation reaction and generate free amine groups. The biochemical properties of these amadoriase enzymes and their role in protein deglycation are described by Wu, X et al., Arch Biochem Biophys. 419(1):16-24 (2003). Sec also Takahasi, M. et al., J. Biol. Chem. 272, 343743 (1997). The amadoriase enzymes are particularly useful since they have strong anti-glycation activity, and some of these compounds are selective for collagen. This makes these enzymes particularly useful as components in the topical formulation of the present invention since they will preferentially act on collagen and therefore inhibit the glycation of collagen and reduce the signs of aging in the skin.

Another class of AGE inhibitors that may be used in the formulation of the present invention is described by Rahbar et al., Molecular Cell Biology Research Commun. 3, 360-66 (2000). These compounds are benzoic acid derivatives, aryl and heterocyclic ureido compounds, and aryl and heterocyclic carboxamido phenoxy isobutyric acids. They have been shown to be potent inhibitors of glycation, and have been shown to inhibit the glycation of collagen. The compounds described by Wu, Takahasi, or Rahbar may be used in combination with the formulation described herein.

Other AGE inhibitors may be added to the formulation of the present invention. Extracts of *Paeonia suffruticosa* have been shown to be AGE inhibitors (Okano et al., at www.creative-developments.co.uk/papers/Natural %20Ingredients %201998.html)-. Additionally, AGE inhibitors have been isolated along with compounds having antioxidant activity from *Paeonia suffruticosa*; these compounds include the monoterpene glycoside, α-benzoyloxypaeoniflorin, β-benzoyloxypaeoniflorin, paeonolide, paeoniflorin and mudanpioside H. (Ryu G., et al, Arch Pharm Res. 2001 April; 24(2):105-8). Another AGE inhibitor is from extracts of *Sanguisorba officinalis*, which has been shown to reduce chronic photodamage to the skin. (Tsukahara K., Biol Pharm Bull. 2001 Sep.; 24(9):998-1003). *Pterocarpus marsupium* has been shown to be an anti-diabetic agent and strong antihyperglycemic agent (Babu P S., J. Pharm Pharmacol. 2004 November; 56(11):1435-42). *C. Cochinchinense* has been found to be a particularly potent AGE inhibitor on proteins and also to strongly inhibit hypochlorous acid-induced DNA damage. (Tang S Y, Free Radio Biol Med. 2004 Jun. 15; 36(12):1575-87).

There are other natural products that are AGE inhibitors, which may be used in the present invention. The screening method described by Matsuura, based on a fluorometric analysis, may be used to determine the inhibitory index of the Maillard reaction and AGE inhibition to determine compounds useful to include in the formulation of the present invention. (Nobuyasu Matsuura et al. J. Health Science 48(6) 520-526 (2002)).

ATP-Enhancing or Encouraging Agents

Cunning is a betaine that is an ATP-encouraging agent and is required for the transport of long-chain fatty acids, ATP production, and removal of excess short- and medium-chain fatty acids. It is derived from the amino acid lysine. L-carnitine is the only biologically active isomer; however, the derivative acetyl-L-carnitine may also be used as the ATP enhancing agent. Acetyl-L-carnitine enters cells and crosses the blood brain barrier more effectively than L-carnitine (Kidd, P. M. 1999 Alt. Meet Rev. 4, 144-161).

Acetyl-L-carnitine has a three pronged anti-aging effect by being a mitochondrial energy boosting agent, helping to boost acetyl-choline necessary for proper face muscle tone and being an effective antioxidant. It is useful in the transport of long-chain fatty acids into the mitochondrial matrix, transport of short- and medium-chain fatty acids away from the mitochondrial matrix, and regulation of energy metabolism through the modulation of acetyl CoA:CoA ratios. For this regulation, the acetyl group of acetyl CoA is transferred to L-carnitine by carnitine acetyl-transferase (CAT), freeing CoA to participate in the PDH reaction. The acetyl-L-carnitine can then be removed from the mitochondria (Arrigoni-Martelli E, et al., Drugs Exp Clin. Res. 2001; 27(1): 27-49; Rebouche C J. Carnitine. In: Shils M E, et al. eds. Nutrition in Health and Disease, 9th ed., Baltimore: Williams & Wilkins; 1999:505-512). This increase of free CoA relative to acetyl CoA enhances the activity of pyruvate dehydrogenase (PDH) which catalyzes the conversion of pyruvate to acetyl CoA, a crucial reaction in glucose metabolism (Ipi.oregonstate.edu/infocenter/othernuta/caraitine/carnitinaefs.html#re-f2). Propionoyl-L, which is not available in the US as an oral supplement, cleaves into L-carnitine and propionate, which is useful as an intermediate during energy metabolism (Brass E. P., et al., J. Am. Coll. Nutr. 1998; 17(3):207-215). Useful carnitines include L-carnitine, acetyl-L-carnitine, propionyl-L-carnitine, acetyl-L-carnitine arginate and dermatologically acceptable salts thereof (e.g., acetyl-L-carnitine hydrochloride and acetyl-L-carnitine arginate dihydrochloride). While meats, fish and dairy provide the richest sources of L-carnitine, it can also be found in tempeh (fermented soybeans), wheat, (0.1 mg/slice of bread), asparagus (0.4 mg/cup), and avocados (2 mg/ea). Generally, oral L-carnitine and acetyl-L-carnitine are available in doses from 500 mg to 2,000 mg/day (Hendler S S, Rorvik D R, eds. PDR for Nutritional Supplements. Montvale: Medical Economics Company, Inc; 2001), and the topical carnitine may be provided in similar or greater doses.

Coenzyme $Q_{10}$ (CoQ10, ubiquinone) is an ATP-encouraging agent that is useful in the present invention. CoQ10 is a naturally occurring compound that is a strong antioxidant and has therapeutic potential for a number of disorders, including congestive heart failure, muscular distrophy, periodontal disease, correction of drug-induced deficiencies, and immune diseases (AIDS, allergies). The biological activity of CoQ10 is believed to be linked to its ability to act as an antioxidant and free radical scavenger protecting the integrity of cell membranes and offsetting the inability of diseased cells to manufacture sufficient energy for cellular repair, by stimulating mitochondrial respiration and production of ATP. It has been shown to be effective in both clinical and cosmetic applications. The solubility and bioavailability of CoQ10 used in the present invention can be enhanced by the method described in U.S. Pat. No. 6,632,443. In one embodiment, 10-300 mg CoQ10 is added to the formulation. In one particular embodiment of the invention, CoQ10 is all-trans CoQ10, as this form occurs naturally in human metabolism. This can minimize the side effects and risks seen with the cis-form or cis-trans mixture. Trans-CoQ10 is available from Kaneka Corp. Japan as KANEKAQ10. This material is used in the nutraceutical industry and is novel in its use for topical application. One particular embodiment combines delta tocotrienols with all-trans Cog10 for synergy, as delta tocotrienol is known to increase the endogenous production of CoQ10.

Coenzyme A (CoA) is an important ATP enhancing agent. CoA is a carrier of acetyl and acyl groups and is essential for numerous biosynthetic, energy-yielding, and degradative metabolic pathways. CoA is associated with the first step of the Krebs cycle, in which an acetyl group is introduced into the cycle. Acetyl-CoA is the common cellular currency for acetyl transfers and has been used in the nutraceutical industry. CoA is derived from adenine, ribose, and pantothenic acid. The CoA precursor, panthethine, which is a vitamin of the B complex, may also be used as an ATP-enhancing agent of the present invention. Panthethine is manufactured by Daichi Fine Chemicals, Inc. as Pantesin LQ80.

Myocontracting Agents

In some embodiments, a myocontracting agent may be combined with the *macqui* berry. Myocontracting agents include, but are not limited to, choline and acetylcholinesterase inhibitors. Some particular agents include huperzine, cerberin, eburnamonine, guanidion, histamine, leonurine, monocrotaline, panaxin, plumbagin, serotionin, solanine, solasanine, and theobromine.

Anti-Edema Ingredients

Edema is defined as soft tissue swelling due to expansion of the interstitial volume. Agents that reduce edema are also useful as agents in the topical formulation of the present invention. Proanthocyanidins which affect blood vessels have been reported in double-blind research to reduce the duration of edema after face-lift surgery (Baroch et al. Ann Chir Polast Esthet 29:393-5 (1984)).

Lipolytic Ingredients

Lipolytic agents may also be applied as part of the topical formulation of the present invention. Theophyline is an agent useful as a lipolytic agent; it acts as both a localize diuretic and a lipolytic agent. Quinolinic acid, a structural analogue of nicotinic acid, inhibits phosphodiesterase activity in adipocytes to increase AMP concentration and increase lipolytic intensity. Other lipolytic ingredients useful in the topical formulation of the present invention include cayenne, *Coleus Forskohlii*, banaba extract, gugulsterone E & Z, bioprene, quinolinic acid, 3-n-butyl-phthalide, adenosine, ajoene, alginates, allicin, alliin, amellin, bergapten, β-ecdysone, bromelain, chebulinic-acid, crocetin, cynarin, diallyl-disulfide, diallyl-sulfide, diallyl-trisulfide, dipropyl-disulfide, forskolin, ginsenoside-rb-2, imperatorin, inulin, nicotinic-acid, opc, opcs, oxypeucedanin, phellopterin, polydatin, resveratrol, s-allyl-cysteine-sulfoxide, s-methyl-l-cysteine-sulfoxide, saikosaponin, wogonin, and xanthotoxin.

Cholinesterase Inhibitors and Acetyl-Cholinesterase Inhibitors

Cholinesterase (ChE) and acetyl-cholinesterase inhibitors (AChE) are partially useful as a component in the topical formulation of the present invention because of their ability to augment the restoring of a youthful tone to the skin.

The ChE inhibitor is preferably obtained from a plant source. Preferred ChE inhibitors include, for example: (+)-carvone, demissine, 1-carvone, solanidine, 1,8-cineole, ephedrine, limonene-oxide, solanine, actinidine, eseramine, lycorine, solasodine, allicin, eseridine, palmatine, thymol, α-chaconine, fenchone, physostigmine, vasicinol, β-2-chacocine, galanthamine, pulegone, bufotenine, huperzine-a, sanguinarine, d-carvone, huperzine-b, selagine, demissidine, ibogaine, and serotonin.

AChE inhibitors are preferrably obtained from a plant source. Some preferred AChE inhibitors are: (+)-menthol, berberastine, huperzine-s, menthone, (+)-piperitenone-oxide, berberine, isomenthol, p-cymene, (+)-pulegone, carvone, isomenthone, piperitenone, 1,8-cineole, chelerythrine, isopulegol, pulegone, akuammicine, d-carvone, 1-carvone, sanguinarine, akuammidine, d limonene, 1-limonene, terpinen-4-ol, alpha-terpinene, elemol, 1-menthol, viridiflorol, (+)-menthol, galanthamine, limonene, yohimbine, (+)-piperitenone-oxide, gamma-terpinene, menthol, menthone, Preferably, the cholinergic substance is obtained from a plant source. Some preferred cholinergic substances are: arecoline, choline, deoxypeganine, deoxyvasicinone, eseridine, galanthamine, iridin, irigenin, lecithin, lithium, nicotine, nobiletin, physostigmine, pilocarpine, pronuciferine, and yohimbine.

Huperzine, an alkaloid derived from the herb Huperzia Serrata, is a preferred inhibitor of acetylcholinesterase (AchE) used in the present invention. Huperzine is useful in the forms huperzine A, huperzine B, 6-β-hydroxy huperzine A, and tautomers thereof. Transdermal application of huperzine has been shown to improve memory and cognitive functions by adding huperzine with a permeation enhancer to increase blood plasma levels of huperzine. (U.S. Pat. Pub. 2004/020705). Similarly, huperzine can be administered topically for the treatment of Alzheimer's disease (U.S. Pat. No. 6,352,715) and cholinergic deficient disorders (WO 2004 080436). In a preferred embodiment, the huperzine-a in the topical formulation is encapsulated in a liposome or nanosome.

Cytidine 5'-diphosphocoline, also known as citicoline or CDP-choline, is a preferred AchE inhibitor. Citicoline, or a stabilized form thereof (see U.S. Pat. Nos. 3,687,932 and 6,057,301), may be used.

Galanthamine is a reversibly acting cholinesterase inhibitor and an acetylecholinesterase inhibitor; it is a tetracyclic alkaloid which was initially isolated from *Galanthus nivalis*. Galanthamine has unique specific properties, for example, highly analgesic effects comparable to those of morphine, and is not as toxic as cholinesterase inhibitors such as physostigmine and neostigmine. The principal use in humans has been the postoperative reversal of neuromuscular blockade. It has also been administered in a number of neuromuscular diseases, and has been shown to enhance activation of motor nerve terminals stimulated electrically, to increase ganglionic depolarization induced by acetylcholine, and to protect against hexamethonium, indicating enhancement of the activity of nicotinic receptors (U.S. Pat. No. 6,670,356). Galanthamine may be isolated, for example, by the process described in U.S. Pat. Nos. 6,617,452 and 6,573,376, from either biological or synthetic material.

Glutathione

Glutathione, reduced glutathione, glutathione peroxidase, glutathione s-transferase or glutathione reductase may be incorporated in the formulation of the present invention. Additionally, synergistic intracellular glutathione inducers and precursors of glutathione may be used. These include omithine, α-ketoglutarate, 1-cystein, 1-glycine, 1-glutamatic acid, glycyl-1-glytamine, n-acetyl-cystein, riboflavin, vitamin B6, parsley seed or seed extract, sylimarin, and cysteine whey peptides. Other ingredients synergistic with glutathione or glutathione precursors which may be added to the formulation include selenium salts, amino acid chelates (including methyl-1-selenocysteine, I-selenomethionine) and sacharomyces selenium ferment, polyenylphosphatidyl-choline, myristicin (which may be isolated from parsley), dihydromyristicin, quercetin, riboflavin, purselane extract, spinach extract, N-acetyl-cysteine, n-acetyl-glutamine, n,ndimethylglycine, anthocyanins, pycnogenol (pines maritime) extract, grape seed extract, turmeric extract, sylimarin, tocopherols, r-lipoic acid, *cynara scolymus* extract, *Picrorhiza kurrooa* extract, *Tinospora cordifolia* extract, *Phyllanthus niruri* extract, *Terminalia belerica* extract, *Terminalia chebula* extract, *Phyllanthus emblica* extract, *Boerhavia diffuse* extract, Defensine (available from Silab), *Phyllanthus amarus* extract, Hibiscus rose sinensis extract, gentisic acid, *Tephrosia purpurea, Andrographis paniculata* extract, *Occinum santum* extract and cysteine peptides. Additionally, SUNACTYL® LS 9610 and AFR® LS 4467/VEG (from Laboratoires serobiologique) may be used.

Glutathione is a tripeptide consisting of the amino acids glutamic acid, cysteine, and glycine. Glutathione is important for the maintenance of the function of enzymes in cell metabolism. It assists in the transport of amino acids across cell membranes. It prevents oxidative alterations of catalytic and allosteric centers, and upholds the optimum conformation of the enzymes for proper functioning (see WO 89/00427). The formation of cataracts is also associated with decreased levels of glutathione. It has been suggested that NADPH production from 1)-glucose aids in glutathione regeneration and protection from mitochondrial dysfunction thereby provide a neuroprotective effect (Delgado-Esteban M, et al., J Neurochem. 2000 October, 75(4):1618-24). U.S. Pat. No. 6,573,299 describes the addition of glutathione in a formulation containing a hydroxy acid. Glutathione has also been shown to be an ACE inhibitor (IC50=3.2 µg/ml), anticytotoxic, antieczemic, antihepatitic, a cancer-preventive, and useful treating heavy metal poisoning. In this formulation, glutathione is particularly useful as it is involved with preventing both oxidative damage and detoxifying RCS (reactive carbonyl species). When skin is exposed to UVB, endogenous is depleted and carrot perform its protective role. Therefore, replenishing can be a crucial step towards preventing photoaging. Furthermore, detoxify RCS such as 4-hydroxynonenal may form adducts with glutathiones and work with the formulation of the invention to reduce the signs of ageing. The combination of glutathione in a topical formulation therefore is particularly useful.

Glutathione peroxidase catalyzes the reduction of hydroperoxides, such as hydrogen peroxides, by reducing glutathione and protecting the cell from oxidative damage. Most glutathione peroxidase enzymes are tetramers having four identical subunits containing selenocysteine in the active site which participates directly in the two-electron reduction of the peroxide substrate. Glutathione is used as an electron donor to regenerate the reduced form of the selenocysteine (Forstrom, J. W., et al., Biochemistry 17, 2639-2644 (1978); Paglia, D. E., Valentine, W. N. J Lab Clin Med 70, 158-169 (1967). Glutathione peroxidase can be added to a topical formulation to protect the skin for oxidative damage.

Glutathione also affects melanin in the skin. Melanin, or skin pigment, is produced by melanocytes. There are two common types of melanin in hair, eumelanin, which is brown/black in color, and phaeomelanin, which is red/yellow in color. Glutathione has been implicated in the biogenesis of the melanin precursor 5-S-cysteinyldopa and the melanogenic activity of pigment cells. Along with cysteine (which is used for glutathione biosynthesis), glutathione will effect the melanin and therefore coloration of the skin (Benathan M. et al., Cell Mol Biol (Noisy-le-grand). 1999 November, 45(7):981-90). Further, glutathione-reductase plays an important role in the regulation and control of the biosynthetic activity of melanocytes. The differences in the glutathione and the glutathione enzyme content in eumelanin and phaeomelanin pigmentation in skin indicate that the increase of glutathione reductase activity in the environment of the melanocytes may stimulate the pigment cells to produce phaeomelanin instead of eumelanin pigment (Benedetto J P et al., J Invest Dermatol. 1982 December 79(6):422-4). Skin with no active melanocytes shows glutathione levels intermediate between those of eurnelanin and phaeomelanin. This is consistent with glutathione reductase activity playing an important role in the regulation and control of the biosynthetic activity of melanocytes. (Benedetto J P, et al., Invest Dermatol. 1981 November, 77(5): 402-5).

Glutathione also affects hyperpigmentation of the skin. Hyperpigmentation, caused by inflammatory skin disorders such as eczema, allergic contact dermatitis, and irritant contact dermatitis acne, is often treated using sunscreen and an agent such as a hydroquinone, tretinoin, azelaic acid, or kojic acid (Pathak M A, Fitzpatrick T B, Nghiem P, Aghassi D S. Fitzpatrick T B, Editor. Dermatology in General Medicine, 4th ed, New York: McGraw-Hill, pp 2742-60 (1993). Glutathione plays a key role in the depigmenting and melanocytotoxic action of these agents, which act to decrease intracellular glutathione by stimulating pheomelanin rather than eumelanin, and thereby lighten hyperpigmentation of the skin. (Alena F, et al., Invest Dermatol 104(5):792-7 (1995)). Therefore, the use of the topical formulation of the current invention can be used to treat hyperpigmentation as well as affect the signs of aging.

Antioxidants

In particular, preferred embodiments, in addition to the antioxidants present in the *macqui* berry, additional antioxidants may be added to the topical formulation of the present invention. Exemplary antioxidants include, but are not limited to, amino acids (e.g. glycine, histidine, tyrosine, and tryptophan) and their derivatives, imidazoles (e.g. urocanic acid) and their derivatives, carotenoids (e.g. lutein, lycopene), carotenes (e.g. α-carotene, β-carotene, lycopene, canthaxantin, cryptoxanthin, zeaxanthin and astaxanthin) and their derivatives, chlorogenic acid and its derivatives, aurothioglucose, propylthiouracil, thiotaurine and other thiols (e.g. thioredoxin, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, aminoethylcysteine, decarboxylated dimmer of aminoethylcysteine ketimine, dilauryl thiodipropionate, distearyl thiodipropionate, thiodipropionic acid and their derivatives (esters, ethers, peptides, lipids, nucleotides, nucleosides and salts) and sulphoximine compounds (e.g. buthionine sulphoximines, homocysteine sulphoximine, buthionine sulphones, pentathionine sulphoximine, hexathionine sulphoximine, heptathionine sulphoximine) in very low, acceptable doses (e.g. pmole to μmoles/kg); also (metal) chelating agents (e.g. α-hydroxy fatty, acids, palmitic acid, phytic acid, lactoferrin, tannins, and curcumine), α-hydroxy acids (e.g. citric acid, lactic acid, malic acid, mandelic acid), humic acid, colic acid, colic extracts, bilirubin, biliverdin, EDTA, EGTA and their derivatives, unsaturated fatty acids and their derivatives (e.g. γ-linolenic acid, linolic acid, oleic acid), folic acid and their derivatives, ubiquinone and ubiquinol and their derivatives, vitamin A and derivatives (e.g. vitamin A palmitate), the B vitamins and their derivatives, coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (e.g. ZnO, $ZnSO_4$) including zinc amino acid chelates (zine-methionine, zinc acetylmethionate), selenium and its derivatives (e.g. selenium methionine), stilbenes and their derivatives (e.g. stilbene oxide, trans-stilbene oxide), proanthocyanidins, ascorbic acid, particularly fat-soluble fatty acid esters of ascorbic acid (e.g. ascorbyl palmitate and tetrahexydecyl ascorbate), quercetin and its derivatives (e.g. quercetin glycoside or rutin), hesperidine, sylimarin, sylibin, glabridin, superoxide dismutase and their derivatives, catalase and its derivatives, carnosic acid and its derivatives, apigenin and its derivatives, luteolin and its derivatives, chlorogenic acid and its derivatives, caffeic acid and its derivatives, ferrulic acid and its derivatives, resveratrol and its derivatives, green tea polyphenols and its derivatives, matrix metalloproteinase inhibitors (e.g. green tea polyphenols, trans-retinoic acid, luteoline, quercetine, ursolic acid, shark cartilage preparations, diterpenes and ursolic acid from *Siegesbeckia* and *Centaurium* extracts, and a tocopherol), Coenzyme Q10, glutathione and its derivatives, myristicin, changkil saponins (from platycodon grandiflorium, which is also known as jie geng), pomengranate, ellagic acid, honokiol (from *magnolia officinalis*), magnolol (from *magnolia officinalis*), naringenin, clove essential oil, martynosides, verbascosides, wolfberry (from *lycium barbarum*) extracts, cascading antioxidants including but not limited to carnosic acid, standardized extract of *Phyllanthus emblica* (trade named Emblica), *pinus* maritime and *pinus* radiate bark extracts, hydroxytyrosol (from olives), genistein, thiotaurine, antioxidants from marine species (e.g., Bioplasma® and monostrama extract from Secma), roxisomes (from AGI), crocetin, pine pollen extracts, beta glucans and the suitable derivatives of the invention (salts, esters, ethers, sugars, nucleotides, nucleosides, peptides and lipids) of these said active ingredients.

Anthocyanins in addition to the anthocyanins in the marque berry may be added to the formulation of the present invention. These anthocyanins may be obtained from any portion of various plant sources, such as the fruit, flower, stem, leaves, root, bark, or seeds. One of skill in the art will understand that certain portions of the plant may contain higher natural levels of anthocyanins and, therefore, those portions are preferably used to obtain the desired anthocyanins. Methods to determine whether and which portions of a plant contain anthocyanins are known and not discussed herein. The extraction and identification of various anthocyanins are described, for example, in U.S. Pat. Nos. 6,818,234, 6,780,442, and 4,413,004. Particularly preferred anthocyanins are derived from natural sources having high anthocyanin content. Approximately 300 anthocyanins have been discovered in nature, and come from sources including, but not limited to, acai berries, *aronia* berries, apples, bilberries, black carrots, blueberries, cherries, cranberries, eggplants, elderberries, grapes, purple carrots, purple loosestrife, purple rice, radishes, raspberries, red cabbage, redcurrants, red-fleshed potatoes, red raspberries, red onions, species from the *Rubus* class (e.g., black raspberry, blackberry, and youngberry), species from the Ribus class (e.g., black currant and gooseberry), sea buckthorn, wolfberry extract, and strawberries.

Preferred anthocyanins that may be added to the formulation of the present invention include anthocyanis found in the extracts of red, blue, purple, magenta and black flowers. These flowers include, but are not limited to purple dahlias, blue lotus, black tulips, and black orchids. Therefore, in one preferred embodiment, the formulation includes an extract of purple dahlia, an extract of black tulip, an extract of black orchid, or a combination thereof.

In one embodiment, an additional antioxidant included in the formulations of the present invention is one or more betacyanin. Betacyanins, like anthocyanins, may be obtained from natural sources and are antioxidants. One betacyanin of interest is betanin found in beets.

A lipoic acid is a preferred antioxidant for use in the topical formulation of the present invention. Lipoic acid is available in both the R and S forms. R-lipoic acid is a preferred form. Furthermore a form of R-Lipoic acid is preferred that does not readily polymerize such as R-lipoic nicotinate and certain sodium salt preparations of R-lipoic acid. The lipoic acid of the present invention also includes the reduced form, or dihydrolipoic acid. In aqueous systems, both lipoic acid and DHLA show strong antioxidant activity. Lipoic acid is also useful in treating diseases associated with oxidative stress including liver cirrhosis, atheroschlerosis, and polyneuritis of diabetes mellitus. (Maitra, I., et al., Free Rad. Biol. Med. 18:823-829 (1995), introduction). The antioxidative activity of lipoic acid is due, at least in part, to its ability to prevent free radical damage to cells and cell components. Free radical damage is most evident in cellular membranes because of the density of the molecular structure of the membranes. (R)-Lipoic acid has been shown to reverse the age-related decline in oxygen consumption and increase mitochondria membrane potential. The age-related decline in hepatocellular glutathione and ascorbic acid levels is reversed by treatment with (R)-lipoic acid (as an oral supplement in rats) (Hagen T M, et al., FASEB J. 1999 February; 13(2):411-8).

Reduced R-lipoic acid, or R-dihydrolipoic acid (R-DHLA), may be used instead of or in addition to R-lipoic acid. R-DHLA which is formed in situ by the reduction of R-lipoic acid by NADH has more antioxidant properties than lipoic acid. Both DHLA and lipoic acid have metal-chelating capacity (LA chelates $Fe^{2+}$ and $Cu^{2+}$; DHLA chelates $Cd^{2+}$) and can scavenge reactive oxygen species. However, only DHLA can regenerate endogenous antioxidants and repair oxidative damage. DHLA can regenerate the endogenous antioxidants vitamin E, vitamin C and glutathione as well as provide peptide methionine sulfoxide reductase with reducing equivalents. The reducing equivalents help in the repair of oxidatively damaged proteins such as a-i antiprotease (Biewenga G P., et al., Gen Pharmacol. 1997 Sep.; 29(3):315-31). DHLA is a potent sulfhydryl reductant and has also been shown to act as a strong direct chain-breaking antioxidant which may enhance the antioxidant potency of other antioxidants such as ascorbate and vitamin E (Kagan V E, et al., Biochem Pharmacol. 1992 Oct. 20; 44(8):1637-49).

Retinol and its derivates such as retinyl palmitate and trans-retinoic acid as well as retinols stabilized in liposomes and cyclodextrin preparations may be added to the present invention. One retinol derivate of interest is tocopheryl-retinoate available from Nikko Chemicals Co. LTD.

Other agents useful in the topical formulation of the present invention include vitamin C and the vitamin C derivatives including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C, such as camu berry (*Myrciaria dubia*), acerola, emblica officinalis, and bioflavonoids from rose hip and citrus, may be used including watersoluble bioflavonoids such as hesperidin methyl chalcone.

In one particularly preferred embodiment, the antioxidant is superoxide dismutase (SOD) (and derivatives), catalase (and derivatives), or a mixture thereof. In a particularly advantageous embodiment, SOD is heterologous SOD (HSDs), described in U.S. Pat. No. 6,426,068, which no longer, or practically no longer, exhibit dismutase activity, but which have conserved their immuno-redox activity, stimulate the production of endogenous SOD, as well u the production of catalase and of glutathione peroxidase. In another embodiment, the *macqui* berry formulation contains a SOD and a lipid or protein such as ceramides, prolamines or polymer films based on prolamines (see U.S. Pat. No. 6,045,809). According to another advantageous embodiment of said use, said plant heterologous SOD is in particular derived from melon. The preferred embodiment uses an encapsulated SOD.

Sesame (*Sesamum indicum*) or sesame lignan may also be added to the present invention. Sesame and its lignans (the fibrous compounds associated with the sesame) act as antioxidants, reduce inflammation, normalize blood pressure, improve lipid levels, and promote fat burning. Sesame has also been shown to aid in the oxidation power or bioavailability of fish oil and conjugated linoleic acid, to enhance the anti-inflammatory effects of essential fatty acids, lower total cholesterol and low-density lipoprotein (LDL), block oxidative damage implicated in atherosclerosis, and reduce blood pressure. Sesame lignans can dramatically increase tissue and serum levels of the vitamin E fractions α tocopherol and γ tocopherol, thereby enhancing their protective properties. (Yamashita K, et al., J Nutr. 1992; 122(12):2440-6). Studies have shown that sesame can also reduce inflammatory processes known to promote cancer, senescence, and aging.

Sesame seed lignans significantly enhance vitamin E activity and increase a tocopherol concentrations in the blood and tissue of rats fed a diet containing a tocopherol and sesame seed or its lignans (Yamashita K, et al., Lipids. 1995 Dec.; 30(11):1019-28). Additionally, they elevate gamma tocopherol concentration by inhibiting an enzyme involved in breaking down tocopherols and tocotrienols (Ikeda S, et al., J Nutr. 2002 June; 132(5):961-6).

Other preferred antioxidants which may be incorporated in the formulations of the present invention include tocopherols (e.g. d-α-tocopherol, d-β-tocopherol, d-γ-tocopherol, d-δ-tocopherol), tocotrienols (e.g. d-α-tocotrienol, d-β-tocotrienol, d-γ-tocotrienol, d-δ-tocotrienol,) and vitamin E (α-tocopherol acetate). These compounds added to the compounds of the present invention may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated from, for example, wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage (Musalmah M, et al., Asia Pac J Clin Nutr. 2002; 11 Suppl 7:S448-51).

Gamma tocopherol is one particularly advantageous E vitamin since it is capable of quenching reactive nitrogen oxide species such as peroxynitrite and nitrogen dioxide (Boje K M. Front Biosci. 2004 Feb. 1; 9:763-76). Gamma tocopherol and its water-soluble metabolite, gamma-CEHC, have been shown to reduce inflammation by inhibiting prostaglandin E2 (Jiang Q, et al., Proc Natl. Acad Sci USA. 2000 Nov. 10; 97(21):11494-9) and gamma tocopherol administration correlates with a reduced risk from heart disease. (Kushi L H, et al. N Engl J Med. 1996 Jun. 2; 334(18):1156-62).

When a tocopherol or tocotrienol is added to the formulation of the present invention, it is also preferable to add sesame oil (or an extract thereof such as sesaminol, a sesame lignans) due to the enhanced antioxidant effect of the combination (Ghafoorunissa, Hemalatha S., et al., Mol Cell Biochem. 2004 July; 262(1-2):195-202; Yamashita K, et al., Lipids. 2002 April; 37(4):351-8). One preferred formulation contains d-α-, d-β-, d-γ-, and d-δ-tocopherol, d-α-, d-β-, d-γ-, and d-δ-tocotrienol in addition to the sesame lignans. Gamma-tocopherol, followed by S and a tocopherol, has the highest content, with a reduced risk from heart disease. (Kushi L H, et al. N Engl J Med 1996 Jun. 2; 334(18):1156-62).

Vitamin A is a preferred addition to formulations of the present invention because of the increased stability it can impart to lipoic acids (Segall, A., J Cosmet Sci. 2004 September-October, 55(5):449-61).

In addition, carotenoids, particularly the xanthophyll type, are also preferred antioxidants that can be used in the practice of the instant invention. The xanthopyll type carotenoids include molecules such as lutein, canthaxantin, cryptoxanthin, zeaxanthin and astaxanthin. Xanthophylls protect compounds such as vitamin A, vitamin E and other carotenoids (Demmig-Adamas, B. Biochemica et Biophsyica Acta, 1020:1-24 (1990)). Xanthophylls can be obtained from a multitude of natural sources, or produced as described, for example, in U.S. Pat. No. 5,916,791.

Flavan-3-ols are also preferred antioxidants that may be used in the formulations of the present invention; they belong to a class of nutrients known as the flavonoid family. Particularly preferred flavan-3-ols include the procyanidin mixtures extracted from grape (*Vitis vinifera*) seed. Proanthocyanidins play a role in the stabilization of collagen and maintenance of distill, two critical proteins in connective tissue that support organs, joints, blood vessels, and muscle (Mitcheva et al. Cell Mol Bio 39:4434 (1993); Maffei et al. Arzneimittelforschung 44:592-601 (1994)). Other flavan-3-ols may also be added to the formulation. These include catechin and epicatechin. Procyanidins are the dieters and oligomers of catechin and epicatechin and their gallic acid esters, and are widely distributed in the plant kingdom. Other flavonoids, such as isoflavin β, quercetin, glabridin, red clover, and others described in U.S. Pat. Nos. 5,686,082 and 5,686,367 may also be included in the formulation.

Myristicin, or 3-methoxy,4,5-methylendioxy-allylbenzene, is a non-amore precursor of 3-methoxy-4,5-methylenedioxyamphetamine and may be incorporated in the formulation of the present invention. It can be found in *Myristica fragrens* (Nutmeg) contains approximately 4.0% myristicin and in parsley (*Petroaelinum crispum, Petroselinum hartense, Petroselinum sativum*), which also contains apiol. Parsley has been traditionally used as a diuretic, for colic, indigestion, and intestinal gas. Myristicin has been shown to induce production of a detoxifying, antioxidant enzyme called glutathione S-transferase, in mice (Ahmad H, et al., Biochem Biophys Res Common. 1997 Jul. 30; 236 (3):825-8). Myristicin can cause convulsions and nausea, and is toxic and hallucinogenic if taken in large amounts. However, smaller doses of myristicin have antioxidantive properties. An oral psychotropic dose of myristicin is 400 mg (see Stein U et al., Forensic Sci Ink. 2001 Apr. 15; 118(1):87-90; Meng G Q, et al., Carcinogenesis, 1992 October; 13(10): 1921-3). Parsley, a source of myristicin, may be used in the topical formulation. However, the amount of parsley extract must be limited due to the fact that parsley can cause phototoxic reaction if there is a simultaneous exposure to sunlight. The rash is caused by the psoralen furocoumarin found in the oil extract of parsley, and is present in other plants as well (celery, fennel, parsnips, limes, lemons, and figs) (see Lagey, K, Burns 1995 Nov.; 21(7):542-3; Gruenwald J. PDR for Herbal Medicine. 1st ed. Montvale, N J: Medical Economics; 1998:1023-1024; Smith D M. Practitioner. 1985; 229:673-675; Stransky L, Tsankov N. ContactDermatitis. 1980; 6:233-234). Therefore, an extract containing myristicin and not furocoumarin may be used to provide the antioxidative and protective effect of the myristicin but without the phototoxic reaction when applied to the skin.

Ethyl (EDTA) or other metal chelators are preferred antioxidants that can be included in the formulation. Plant tannins are also metal chelators that may also be included in the formulation of the present invention. The chelating agent forms a complex with metal ions, inactivating them, and preventing them from affecting antioxidant activity. Other chelators, in addition to those described above, include, but are not limited to, dihydroxyethyl glycine, citric acid, tartaric acid, and mixtures thereof.

In one preferred embodiment, a metal chelators is added to the formulation which may or may not include an additional antioxidant. The metal chelating agent is particularly advantageous in that it father stabilizes the color and antioxidant property of the *macqui* berry or *macqui* berry extract and the optional additional antioxidant.

An additional antioxidant that may be used in the present invention is a phenylpropanoid glycoside. Martynoside, a particularly preferred phenylpropanoid glycoside, may be isolated from a number of botanical sources such as: *Clerodendron trichotomum* (appa1.niaid.nih.gov/struct_scarch/); the aerial section of *Scutellaria* panties (Ersoz, T, et al., Turkish J. Chem. "Phenolic Compounds from *Scutellaria pontica*", which also provides the isolation of other phenylalkyloid glycosides); transformed root cultures of *Catalpa ovata* (*Halina* Wysokinaka J, et al., Free Radio Res. 2003 August 37(8):829-33); *Pedicularis plicata* (Liao, R. et al., Phytotherapy Research 1999 13(7):621-623; which also provides the isolation of verbascoside); *Pedicularis* (Wang et al., Sci China C Life Sci (1996) 39(2):154-8; which also provides the isolation of the phenylpropanoid glycosides: echinacoside, verbascoside, leucosceptoside a, and pediculariosides a, m and n). Their antioxidant scavenging activities are similar to those of the o-dihydroxy group of phenylpropanoid glycosides (Wang at al, Biochem Pharmacol (1996) 51(5):687-91). The addition of martynoside or verbascoside as an ingredient in the formulation of the current invention is particularly advantageous because these phenylpropanoid glycosides have been shown to reduce fatigue in muscle tissue. This allows for a relaxation and smoothing in the overlying skin and reduces the signs of aging (Liao, R. et al., Phytotherapy Research 1999 13(7):621-623).

An additional antioxidant that may be used in the present invention is coffee berry. Coffee berry is the fruit from a coffee tree or shrub, and has an ORAC of 6250 mole TE/g. The coffee berry is rich in polyphenols, and contains phenolic acids at a concentration of 97 mg/100 g (Manila, P. et al., J Agric Food Chem. 2006, 54(19):7193-9). In one preferred embodiment, an extract of the whole berry may be added as a additional antioxidant. In other embodiments, extracts containing only part of the coffee berry, with or without the seed, may be used.

Green coffee extracts may also be added to the formulation of the present invention. Hydroxycinnamic acid derivatives (3-caffcoylquinic acid (3-CQA), 4-caffeolyquinic acid (4-CQA), 5-caffeoylquinic acid (5-CQA), 5-feruloylquinic acid (5-FQA), 3,4-dicaffeoylquinic acid (3,4-diCQA), 3,5-dicaffeoylquinic acid (3,5-diCQA), and 4,5-dicaffoylquinic acid (4,5-diCQA)) are found in coffee berry seeds (i.e., green coffee beans). The diCQA hydroxycinnamic acid derivatives have a strong free radical scavenging activity while the other hydroxycinnamic acid derivates also show superoxide anion radical scavenging activity (Iwai K, et al., J Agric Food Chem. 2004 Jul. 28; 52(15):4893-8). U.S. Pat. No. 5,972,409 describes a method of obtaining soluble extract from green coffee. The green coffee extract may be provided from either the whole fruit or the seed. In another embodiment, caffeic acid may be added to the formulation.

In a preferred embodiment, the antioxidant is an antioxidant endogenous to the human body. These antioxidants include, but are not limited to superoxide dimutates (SODs, such as Mn, Zn, or Cu SODs), glutathione and the glutathione enzymes, NADH, lipoic acid and the salts and metabolites thereof, NAC, thioredoxin, and the tocopherols.

The amount of antioxidant in the formulation (added in addition to the anthocyanin) is preferably from about 0.001 to about 80% by weight, preferably from about 0.1 to about 5% by weight, based on the total weight of the preparation.

In one embodiment, the additional antioxidant in the formulation is added in a particular ratio compared to the antioxidant in the *macqui* berry or *macqui* berry extract. The ratio is determine to optimize (i.e., increase) the ORAC value of the formulation containing the two or more antioxidants. This ratio is determined through testing the ORAC values of compositions having various ratios, and may be done by the methods as disclosed by Brunswick laboratories (www.brunswicklabs.com). Assays such as those described by D. Huang et al. in J. Agric. Food Chem. 2005, 53, 1841-1856 and D. Huang et al. in J. Agric. Food Chem. 2002, 50, 44374444 may be used to determine ORAC.

Matrix Metalloproease Inhibitors

Matrix metalloprotease (MMP) inhibitors may also be added to the formulation of the present invention. Most MMPs are thiols or hydroxyamates. Many MMPs are neutral zinc-dependent endopeptidases that selectively catalyze the hydrolysis of polypeptide bonds; they degrade and rebuild structural proteins in collagens and are required for the healing of moist skin wounds (Agren M S. Arch Dermatol Res. 1999 291(11):583-90). Increased concentrations of MMP 1 (collagenase 1, interstitial collagenase), 3, (stromelysin 1), 7 (matrilysin, pump), 9 (gelatinase b, 92kd gelatinase), and 12 (macrophage metalloelastase) have been found in sun-exposed skin. Additionally, increased levels of MMP-1 have been found in smokers (Lahmann C, et al., Lancet 2001, 357:935-936) MMP levels are also known to rise in fibroblasts as a function of age, and oxidant stress is believed to underlie changes associated with both photoaging and natural aging (Varani J, et al., J Invest Dermatol. 2000114(3):480 6). Therefore the addition of inhibitors of MMPs, particularly MMP-1, 3, 7, 9, and 11 in the topical formulation of the present invention, is contemplated. MMP inhibitors include the tissue inhibitors of metalloproteinases (TIMPS) which are the natural inhibitors of MMP activity (Gomez, D E. et al. (1997) Eur. J. Cell Biol. 74:111.), and include compounds such as ilomastat (www.chemicon.com/product).

Anti-Inflammatory Agents

The free radicals associated with aging akin will often also induce inflammation in the akin and lack of skin immunity. Therefore anti-inflammatory agents including NSAIDS, COX-2 inhibitors (e.g., nexrutine, ursolic acid, quercetin, curcumine, and evodia extract) (Kang, S. S., et al., Nat. Prod. Sci., 1999, 5(2): 65-69) can be included in the formulation of the present invention.

Mitochondria) Resuscitants

Mitochondrial resuscitants may also be added to the *macqui* berry formulation. Mitochondria) decay in aging is a major driving force behind the aging process (Ann N Y Acad Sci. 2004 June; 1019:406-11; Proc Natl Acad Sci USA. 1994 91:10771-8). The mitochondria are the powerhouses of the cell responsible for producing all cellular energy and convert carbohydrates and fatty acids into ATP. ATP is necessary for the production of proteins, which declines with aging (e.g., collagen and elastin).

Agents useful as mitochondria) resuscitants include, but are not limited to, lipoic acid (Ames B., Ann. N.Y. Acad. Sci. 1033: 108-116 (2004), carnitine, COQ10, CoA, NADH, FADH, succinic acid, creatine, Dubose, 5-phosphoribosyl-1-pyrophosphate (PRPP), Sepitonic M3® (containing magnesium aspartate, zinc gluconate, copper gluconate), pyruvate, phosphoglycolipids, gymnostemma *pentaphyllum*, and cytochrome C. Additionally, agents including phenylbutylnitrone (PBN) and other spintraps, such as the nitrone or nitroso spin traps described in U.S. Pat. No. 5,723,502 (N-t-butyl-α-phenylnitrone, 3,5-dibromo-4-nitrosobenzenesulfonic acid, 5,5-dimethyl-1-pyrroline N-oxide, 2-methyl 2-nitrosopropene, nitrosodisulfonic acid, α-(4-pyridyl-1-oxide)-N-t-butylnitrone, 3,3,5,5-tetramethylpyrroline N-oxide, and 2,4,6tri-t-butylnitrosobenzene) as well as hydroxylamines such as N-bat-butyl hydroxylamine may be used. These agents are antioxidants as well as mitochondria) resuscitants.

D-ribose is a naturally occurring five-carbon sugar found in all living cells, and is a preferred mitochondria) resuscitant. It is not an essential nutrient, since it can be made in the body from other substances, such as glucose. ATP (adenosine triphosphate) requires D-ribose, as do nucleotides, nucleotide coenzymes, and RNA (ribonucleic acid). D-ribose, in the form of ribonucleoside diphosphates, is converted to deoxyribonucleoside diphosphates, precursor molecules for DNA. D-noose in RNA and D-deoxyribose in DNA. When D-ribose is added to the formulation, it is particularly preferred to additionally include an AGE inhibitor to prevent the potential glycating effect of d-ribose.

R-lipoic acid is implicated in mitochondria) energy production and protection from free radicals. It has been shown to maintain microsomal protein thiols, protect against hemolysis, protect against neurological disorders, and protect against ischemia/reperfusion injury. R, not S-lipoic acid is produced by the body and decreases in concentration during the aging process (Pick U., et al., Biochem Biophys Res Common. 1995 Jan. 17; 206(2):724-30). The formulation of the present invention replenishes this vital substance as well as provides protection to the skin cells. R-lipoic acid is incorporated in the formulation in one preferred embodiment of the present invention.

Acetyl-L-carnitine has a three pronged anti-aging effect by being a mitochondria) energy boosting agent, helping to boost acetyl-choline necessary for proper face muscle tone and being an effective antioxidant. It is useful in the transport of long-chain fatty acids into the mitochondrial matrix, transport of short- and medium-chain fatty acids away from the mitochondria) matrix, and regulation of energy metabolism through the modulation of acetyl CoA:CoA ratios. For this regulation, the acetyl group of acetyl CoA is transferred to L-carnitine by carnitine acetyl-transferase (CAT), freeing CoA to participate in the PDH reaction. The acetyl-L-carnitine can then be removed from the mitochondria (Arrigoni-Martelli E, et al., Drugs Exp Clin Res. 2001; 27(1): 27-49; Rebouche C J. Carnitine. In: Shils M E, et al. eds. Nutrition in Health and Disease. 9th ed. Baltimore: Williams & Wilkins; 1999:505-512). This increase of free CoA relative to acetyl CoA, enhances the activity of pyruvate dehydrogenase (PDH) which catalyzes the conversion of pyruvate to acetyl CoA, a crucial reaction in glucose metabolism (lpi.oregonstate.edu/infocenter/othemuts/carnitinc/carnitinerefs.html#re-f2).

The *macqui* berry formulation may be combined with a combination of a lipoic acid, a camitine, and a carnosine. The usefulness of a combination having these three ingredients is described in U.S. patent application Ser. No. 11/388,908, herein incorporated by reference.

ATP, adenosine 5'-monophosphate (AMP), and their degradation products may also be administered directly as agents in the topical formulation of the present invention. U.S. Pat. No. 5,227,371 teaches the oral or topical administration of AMP, ATP or their degradation products adenosine and inorganic phosphate to increase ATP levels. Extracellular ATP has been shown to help regulate vascular tone (Burnstock, G. and Kennedy, C Circul. Res. 1986, 58, 319-330), promote muscle contractions (Burnstock, G. Pharmacol. Rev. 1972, 24, 509-581), and arresting tumor growth (U.S. Pat. No. 5,049,372). When ATP or other agents susceptible to degradation are used, a stabilized form of the agent is preferred.

Transforming growth factor-beta (tgf-beta), a potent fibrogenic cytokine has been shown to decreases intracellular glutathione content, and increases collagen I mRNA content and collagen protein production. The effect of glutatione depletion on tgf-beta-stimulated collagen production may be mediated by facilitating reactive oxygen species signaling. (Liu R M et al., Am J Physiol Lung Cell Mol Physiol. 2004 286(1):1121-8.) It is therefore contemplated to additional add tgf-beta to the formulation of the present invention.

Depigmenting Agents

Depigmenting agents may be added as an additional agent in the present invention. Depigmenting agents include tyrosinase inhibitors such hydroquinone and its derivatives (e.g., hydroquinone monomethyl ether, hydroquinone monoethyl ether, arbutin); soy and derivatives thereof, retinoids such as retinol; Kojic acid and its derivatives (e.g., kojic dipalmitate); transexamic acid; vitamins such as niacin, vitamin C and its derivatives; azelaic acid; phytic acid, licorice; mulberry extracts; extracts from *rumex* species such as *rumex crispus* extract; chamomile extracts; green tea extracts; lactic acid, pearl extract, *Tricholoma matsutake* extract, magnesium-asorbyl-phosphate, edelweiss extract, sedum acre extract, arbutine, ergothione, *phyllantus emblica* extract, α-MSH antagonists such as Undecylenoyl phenylalanine, germanium, and GABA and *songyi* mushroom. Bowman-Birk Inhibitors are described in U.S. Pat. No. 6,750,229 (e.g., inhibitors derived from the leguminosae, solanaceae, gramineae or cucurbitaceae family). Dermalight® and Clarisldn3® from Silab are also depigmenting agents that can be used. Kinetin (N6 furfuryladenine) is a 6-(R-amino)purine cytokinin and is described in U.S. Pat. Nos. 5,602,139, 5,164,394, and 5,021,422. It has been shown to have anti-aging effects on the skin of dogs as well as the depigmenting effects without adverse effects (Kimura T, Doi K., Rejuvenation Res. 2004 Spring; 7(1):32-9).

Skin Protective Lipids

Skin-protective lipids, such as ceramides, cerebrosides, essential fatty acids and botanical or marine oils containing these, *calophyllum inophyllum* squalene, squalane, botanical oils and butters such as (shea butter, meadowsweet oil and coconut oil) phospatidylserine, spingolipids and natural materials containing them such as *Conyza Canadensis*, phospholipids and sulfatet sterols available from Vincience may also be added to protect the skin. A particular embodiment comprises a krill oil rich in Omega 3 PUFAs (EPA and DHA) as well as in antioxidants such as vitamin A, E or asthaxanthin. This lipid is particularly suitable for use in the formulation of the present invention due to its multipronged effects including antioxidant action (ORAC value of 378), energy production function and anti-inflammatory action.

Nicotinamide-adenine-dinucleotide (NADH), in its reduced form, is a coenzyme form of vitamin B3 (niacinamide), which occurs in all living cells including human cells. Similarly, nicotinamide-adenine-phosphate-dinucleotide (NADPH) is the phosphorolated form of NADH, and as used herein, NADPH is included in the term "NADH." NADH may be added to the formulations of the present invention.

NADH

NADH stimulates the production of ATP (adenosine triphosphate) during the regulation and release of stored energy. Higher levels of NADH in the cell allow for the release of energy. Because of this, the oral administration has been used to NADH treat fatigue, chronic fatigue syndrome, and fibromyalgia. There is also an indication that NADH may be useful in treating Alzheimer's disease (U.S. Pat. No. 5,444,053), treating Parkinson's disease (U.S. Pat. Nos. 4,970,200 and 5,019,561), depression, improving memory and concentration, and enuurance.

The topical administration of NADH is described in U.S. Pat. No. 5,952,312, which demonstrates that NADH is adsorbed by the skin and stimulates enzymes essential in the production of energy. When NADH is included in the topical formulation, an additional stabilizer which inhibits oxidation of NADH may also be added. The stabilizer is $NaHCO_3$, ascorbic acid, sodium ascorbate, tocopherols, tocopherol acetate, polyvinylpyrolidone, or a combination thereof (U.S. Pat. No. 5,952,312).

The addition of NADH is useful in the formulation of the present invention when lipoic acid or DHLA is incorporated in the formulation because it allows for the conversion of R-lipoic acid into the more active DHLA. As DHLA works to remove the signs of aging in the skin, it is oxidized to the less effective R-lipoic acid. NADH will then reduce the lipoic acid to form DHLA, which then continues to remove the signs of aging. In formulations of the present invention, the addition of NADH is also useful because DHLA will be converted to lipoic acid upon contact with an oxidizing species in the skin; the NADH then effectively converts the lipoic acid back to DHLA. In one preferred embodiment, the topical formulation of the present invention contains NADH (or NADPH) at a concentration of 0.1%40%, or more preferably 1%-5%.

Sunscreen Agents

In some embodiments, an additional active ingredients included in the formulations of the present invention are compounds having sunscreening action. Sunscreening agents include, but are not limited to aminobenzoic acid, avobenzone, dioxybenzone, homosalate, lisadimate, menthyl anthranilate, octocrylene, octyl methoxycinnamate, octyl salicylate, oxybenzone, padimate o, phenylbenzimidazole, roxadimate, sulisobenzone, titanium dioxide, trolamine salicylate, zinc oxide, hammamelitannin, and combinations thereof (see www.nlm.nih.gov/medlineplus/druginfo/uspdi/202782.html). In one particular embodiment, the sunscreen agent or agents are naturally occurring substances such as zinc oxide, coffee oil, leuco-melanin, date palm fruit melanin, and galanga extract (available from symrise). Other substances that protect from uv damage that may be used include such as *sanguinaria* extract *krameria triandra* root extract (15% neolignans) metallothionein, 1,25-dihydroxyvitamin d3, and thymidin dinucleotide. A preferred sun-protective extract is a *polypodium leucomotos* extract. This compound may be incorporated in the topical formulation or, alternatively, it may be provided as an oral supplement in addition to the formulation of the present invention for increased protection from UV damage (Middlekamp-hup et al, J Am Acad Dermatol, 2004, 51(6) 910-918). One preferred sunscreen agent is isoamyl-p-methoxycinnamate (from galanga, available from symrise, GMBY & Co.); this compound provides an spf of greater than 30 using only natural ingredients (botanicals, antioxidants, coffe oil and microfine zinc oxide). Additional sunscreen agents include allantoin, aloesin, apigenin, caffeic-acid, chlorogenic-acid, ellagic-acid, esculetin, esculin, ferulic-acid, fraxetin, fraxin, lawsone, p-aminobenzoic-acid, paba, procyanidins, rutin, silymarin, squalene, and umbelliferone.

Anti-Erythema Ingredient

By adding an anti-erythema ingredient to the formula, an additional effect caused by the damaging UV radiation besides free radical formation, is addressed. The reduction in redness accomplished by applying the formulation of the present invention is due to an incorporation of aesculin, colchicines, esculin, glycyrrhetinic-acid, opc, opcs, procyanidin-a-2, procyanidins, rutin, or silymarin into the formulation. Silymarin is a mixture of at least 4 closely related flavonolignans, 60 to 70% of which is a mixture of 2 diastereomers of silybin. It has been shown to increase patient serum levels of glutathione and glutathione peroxidase. It also works to increase superoxide dismutase (SOD) activity of lymphocytes and erythrocytes, as well as the expression of SOD in lymphocytes. Silymarin has been administered orally at a dosage of 420 mg/day. (Wellington K, Jarvis B, BioDrugs. 2001; 15(7):465-89).

Agents for Hormonal Decline

Hormonal decline is known to occur with aging; therefore a class of substances replenishing and regulating these is useful in combination with the *macqui* berry formulation of the present invention. A non-exclusive list of agents useful for treating hormonal decline is estriol, 7-keto-dhea, dhea, estrone, estradiol, progesterone, pregnenolone, melatonin, soy isoflavons, phytoestrogens (back cohosh, red clover, sage, etc.), chrysin, diosgenin, *vitex* extract, diindolmethane, *pueraria mirifica* (puresterol available from bio-botanica), β-sitosterol, β-stigmasterol, betulin and derivatives thereof, *conyza canadensis* essential oil, and maca extract standardized to macamides.

Anti-Acne Agents

Anti-acne agents may also be combined with the formulation of the present invention. Since both free radicals and inflammation are cofactors in acne, especially in adult skin, a combination with one or more anti-acne ingredient may be used in the topical formulation of the present invention. A non-limiting list of useful anti-acne agents includes (−)-epigallocatechin, (−)-epigallocatechin-gallate, α-pinene, α-terpineol, anacardic-acid, azelaic-acid, baicalein, berberastine, berberine, β-carotene, camphor, caryophyllene, cryptotanshinone, 5-cadinene, γ-linolenic-acid, indole, linoleic-acid, nerolidol, pufa, pufas, pyridoxine, resorcinol, selenium, sulfur, terpinen-4-ol; thymol, tin, and zinc.

Anti-Cellulitic Agents

Compounds having anti-cellulitic activities may be included as an additional ingredient in the formulation of the present invention. These compounds include, but are not limited to, aesculin, bromelain, esculin, theobromine, and theophylline. Additional anti-cellulitic compounds include caffeine, di-indolmethane, anti-estrogenic botanicals, *terminalia arjuna, garcinia cambodgia*, dihydromyricetin as found in Myriceline by Provital, as well as a citrus aurantium extract (see U.S. Pat. No. 6,224,873). This compound does not cross the blood/brain barrier and has minimal impact on α 1,2 and β1,2 receptors, and is therefore safer then caffeine, and/or ephedra containing agents. In one embodiment, no stimulants having a systemic effect if absorbed into the bloodstream are incorporated into the formulation.

Anti-Edemic Agents

Compounds having an anti-edemic activity are useful in combination with the formulation of the present invention. The prevention of swelling and fluid retention in the skin present in both face and body can be aided by combining an agent such as one of the following to the compound of the present invention. These compounds include, but are not limited to, (e)-4(3',4'-dimethoxyphenyl)-but-3-en-ol, 10-acetoxy-8-hydroxy-9-isobutyloxy-6-methoxythymol, 13',ii8-biapigenin, 4-vinyl-guaiacol, 7-methoxycoumarin, acetyl-11-keto-β-boswellic-acid, actinidoles, aescin, α-amyrin, amentoflavone, anagyrine, anisodamine, anthocyanoside, arbutin, aristolochic-acid, aromaticin, artemetin, ascorbic-acid, asiaticoside, astringenin, aucubin, baicalein, baicalin, bavachinin, berberastine, berberine, β-aescin, β-amyrin, β-boswellic-acid, β-damascenone, β escin, β-sitosterol, betulinic-acid, boehmerol-acetate, boldine, boswellic-acid, bradykininase, brazilin, bromelain, caffeic-acid, caryophyllene, caryophyllene-oxide, catechin, cis-spiroether, coniferyl-aldehyde, coumarin, crotaloburine, cryptolepine, curcumin, damascenine, digitoxin, diosmin, ephedrine, ephedroxane, escin, eugenol, eupahyssopin, faradiol, faradiol-monoester, friedelan-3-β-ol, gentianine, gentiopicroside, germacrone, ginkgetin, ginsenoside-r-o, glucose, glycyrrhetic-acid, glycyrrhetinic-acid, glycyrrhizin, gnaphaliin, hederagenin, helenalin, humulone, isoferulic-acid, kawain, lanceolarin, lapachol, lupeol, madecassoside, maslinic-acid, matricine, matrine, oleanolic-acid, opc, opcs, oxoushinsunine, paeonol, pepsin, papaverine, piperine, proanthocyanidins, procyanidin, procyanidins, pseudoephedrine, quercitrin, resveratrol, rosmarinic-acid, rutin, saikogenin, saikosaponin, sanguinarine, sciadopitysin, scopoletin, serrapeptase, aldehyde, strophanthidin, syringaldehyde, taraxasterol, taraxasterol-acetate, taspine, tylophorine, umbelliferone, ursolic-acid, and withaferin-a.

Anticapillary-Fragility Agents

Compounds having 'anticapillary-fragility' activity may also be included as an additional ingredient. Capillary-fragility causes telangiectasia and spider veins, which are preferably reduced or removed from the skin by using an anticapillary-fragility agent. Further, AGES and free radicals can cause damage to the fine vessels and induce telangiectasia or spider veins; therefore this class of agents is also useful. These agents include, but are not limited to, aescin, aesculetin, aesculetol, aesculin, aesculoside, diosmin, escin, esculetin, esculin, hederagenin, hesperidin, hydroxyethylrutoside, hyperoside, inulicin, luteolol, maniflavone, neoruscogenin, patulin, procyanidin-a-2, quercetol, quercetoside, rhamnetol, ruscogenin, rutin, rutoside, and xanthorhanmoside. Additionally, microcirculation decreases with age, especially around the eyes. Therefore this class is also beneficial and includes hydroxysuccinimide, chrysin(and other bilirubinolytic substances such as gardenin, gardenoside, berberine) or ingredients containing such substances eg Haloxyl from Sederma, Nattokinase, and vitamin K in all its forms including menaquinone-7.

Anti-Elastase Agents

Anti-elastase ingredients are also beneficial as additional ingredients which enhance the formula's ability to firm the skin. These agents include, but are not limited to, PROTEA-SYL® TP LS 8657 (from Laboratories Serobiologique), anthocyanins, caffeic-acid, isoquercitrin, procyanidin-a-2, and quercetin. To help target sagging of skin, these ingredients can be included that improve adhesion of cells to the basement membrane and among themselves by enhancing synthesis of laminin V and integrin alpha 6. One such ingredient is Scrilesine from Lipotec.

Alpha Hydroxy Acids

Alpha hydroxy acids and α-hydroxy acid derivatives, known for their exfoliating and resurfacing properties, may be combined as an ingredient in the topical formulation of the present invention in combination with a saccharide isomerate, green tea, strontium chloride and/or a COX 2 inhibitor to prevent stinging. An a hydroxy acid is an organic compound containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties (e.g., glycolic acid, lactic acid).

Liposomes

A In a preferred embodiment, liposomes made by the process described by AGI Dermatics (New York) may be used. These photosomes and ultrasonics are useful in formulations used to target DNA repair associated with photoaging and are described in U.S. Pat. Nos. 6,623,724 and 6,479,533. A marine-derived photolyase, a DNA-repair enzyme from *Anacystis nidulans* plankton may be added to the formulation. These enzymes, incorporated into a liposome (e.g., Photosome®), are adsorbed through the skin and repair sun-damaged DNA. Redness and sunburn cell formation may also be reduced or prevented by the addition of these enzymes.

Dermorelaxants

Dermorelaxants, which relax the muscles directly beneath the skin, may also be incorporated into the formulation of the present invention. These compounds relax the muscles and reduce wrinkles in the skin. Dermorelaxants include compounds such as myoxinol from cognis, boswellia extract and hexapeptides (available from Lipotech, Spain) and may be incorporated into the formulation of the present invention. Additional dermorelaxants include limonoids such as those described in U.S. Pat. No. 6,866,856. Limonoids are plant alkaloids of the Maliaecae family, such as toosendanin and azadirachtin, that are useful for relaxing the facial expression muscles.

Acetylcholine Precursor

An acetylcholine precursor may be added to the topical formulation of the present invention. An acetylcholine recursor is any precursor in the bio-synthetic pathway of acetylcholine, or related pathways. These include co-factors and precursors of acetylcholine, synthetic enzymes and precursors or enhancers of acetyl production. Useful acetylcholine precursor compounds for the invention include, but are not limited to, ethylaminoethanol, methylaminoethanol, dimethylaminoethenyl, isopropanolamine, triethanolamine, isopropanoldimethylamine, ethylethanolamine, 2-butanolamine, choline, serine, the calcium salt of 2-aminoethanol phosphate, the sodium salt of 2-aminoethanol phosphate, the potassium salt of 2-aminoethanol phosphate, and mixtures thereof. Many preferred embodiments employ methylaminoaminoethanol, dimethylaminoethanol, ethylaminoethanol, the calcium salt of 2-aminoethanol phosphate, and/or triethanolamine; particularly preferred is dimethylaminoethanol (DMAE) and/or the calcium salt of 2-aminoethanol phosphate.

Additional Agents

Mother particularly preferred skin-protective agent is beta glucan, which may be obtained from yeast, oat and mushroom species. It is a free radical scavenger and stimulates nonspecific immunity.

Hyaluronic acid, a component of connective tissue whose function is to cushion and lubricate the tissue, as well as hyaluronidase inhibitors such as extracts of *Echinacea* species, are also useful as additional agents in the present formulation.

Forskholin and other agents useful in raising cyclic AMP are also contemplated as ingredients in the present formulation.

Lion's mane is included in the formulation in one embodiment. This medicinal mushroom (*Hericium erinaceum*) has been used to treat dementia and contains at least two classes of compounds, erinacines and hericenones, both which strongly stimulate NGF synthesis (Kawagishi, H. et al., Townsend Letter for Doctors and Patients, 4-2004).

The additional agents can be used in the formulation of the present invention, or may be applied separately. The amount of additional agent is dependent upon the activity of that particular agent, and will vary depending upon the preferred formulation. In most instances, each agent will be present in the formulation in an amount from about 0.001 to about 30% by weight, preferably from about 0.1 to about 5% by weight, based on the total weight of the preparation.

In some embodiments, certain agents may be included in the formulation in a homeopathically diluted form due to their potential toxicity or irritating potential. Therefore, these agents may be added at much lower concentrations. These agents would be formulated according to strict homeopathic standards and, depending on the substance, the effect may be the same or different from that of the starting molecule.

Similarly, for highly active agents such as growth factors, the amount of agent added to the formulation may be less than the 0.001% as described above. For these agents, the weight percent may be from 0.00001%, or from 0.0001% and up.

Of the additional agents described herein, 1, 2, 3, 4, 5, 6, 7, 8, 9, 10, or more additional agents may be added. The additional agents may be combined with the topical formulation using any combination that one of ordinary skill in the art would perceive to combine. Two or more additional agents from one category (e.g., two AGE inhibitors) may be added to the same formulation. Since the combination of some of the additional agents may cause adverse effects not outweighed by their positive benefit when topically applied to the skin, care will be taken when making a topical formulation. Data from the FDA, research publications and any other known sources will be used to determine if there are known adverse interactions between any of the ATP enhancing agents and additional agents incorporated in the formulation. Combinations with unacceptable adverse effects will not be used in the topical formulations of the present invention.

IV. Topical Formulations

The formulations of the present invention may also comprise dermatologically acceptable topical carriers. Dermatologically acceptable carriers, also known as auxiliaries, are known in the fields of dermatology, pharmacology, food technology and related fields. In particular, the carriers listed in relevant Pharmacopeia (e.g. DAB Ph. Eur. BP NF), and other auxiliaries whose properties do not impede physiological use when applied to the skin, may be used.

Suitable carriers may be lubricants, wetting agents, emulsifying and suspending agents, preservatives, anti-irritants, emulsion stabilizers, film formers, gel formers, odor masking agents, resins, hydrocolloids, solvents, solubilizers, neutralizing agents, permeation accelerators, pigments, quaternary ammonium compounds, refatting and superfatting agents, ointment, cream or oil base materials, silicone derivatives, stabilizers, sterilizing agents, propellants, drying agents, opacifiers, thickeners, waxes, emollients, or white oils.

Only effective amounts of *macqui* berry or *macqui* berry extract and other optional active ingredients are needed. Generally topical application is accomplished in association with a carrier, and particularly one in which the active ingredients are soluble per se or are effectively solubilized (e.g., as an emulsion or microemulsion). Where employed, the carrier is inert in the sense of not bringing about a deactivation or oxidation of the compounds, and in the sense of not bringing about any adverse effect on the skin areas to which it is applied. In one preferred practice of the invention, active ingredients are applied in admixture with a dermatologically acceptable carrier or vehicle so as to facilitate topical application and, in some cases, provide additional therapeutic effects as might be brought about by, e.g., moisturizing of the affected skin areas. While the carrier for dermatological formulations can consist of a relatively simple solvent or dispersant such as water, it is generally preferred that the carrier comprise a composition more conducive to topical application, and particularly one which will form a film or layer on the skin to which it is applied so as to localize the application in areas that will be electrically stimulated and/or aid in the percutaneous delivery of the active agent.

Many preparations of topical carriers are renown in the art, and include lotions containing oils and/or alcohols and emollients, vegetable oils, hydrocarbon oils and waxes, silicone oils, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. They may be formulated using conventional techniques known to those of ordinary skill in the art.

Additional excipients commonly found in skin care compositions such as, for example, emollients, skin conditioning agents, emulsifying agents, humectants, preservatives, antioxidants, perfumes, chelating agents, buffering agents, etc. may be utilized provided that they are physically and chemically compatible with other components of the formulation. Preservatives include, but are not limited to, $C_1$-$C_3$ alkyl parabens and phenoxyenthanol, typically present in an amount ranging from about 0.5% to about 2.0% by weight percent, based on the total formulation. Emollients, typically present in amounts ranging from about 0.01% to 5% of the total formulation include, but are not limited to, fatty esters, fatty alcohols, mineral oils, polyether siloxane copolymers, and mixtures thereof. Humectants, typically present in amounts ranging from about 0.1% to about 5% by weight of the total formulation include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts front about 1% to about 10% by weight of the formulation, include, but are not limited to, stearic acid, cetyl alcohol, stearyl alcohol, steareth 2, steareth 20, acrylates/$C_{raw}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Buffering agents may be added to provide the formulation with a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

One particular embodiment comprises the use of novel dispersions of hydrophobes to yield a surfactant-free formulation, by subjecting the materials to high pressure, high shear processing. Cold process formulations are also a preferred method as they protect certain heat-sensitive sensitive agents in the formulation; they can be obtained by using self-emulsifying oleosomes such as Natrulon OSF available from Lonza. In one embodiment, the formulation is processed using the carriers and dry-water process of Aerosil® (Degussa), which is based on fumed silica. (see www1.sivento.com/wps3/portal/en/aerosil/industries/personal0.html).

According to the invention, the formulations are administered topically in the form of a cream, gel, or liquid. The topical administration provides the stabilized *macqui* berry formulation directly to the skin, which is preferably provided with the use of a dermatologically acceptable carrier. While the carrier may consist of a relatively simple solvent or dispersant, such as an oil, it is generally preferred that the carrier comprise a material more conducive to topical application, and particularly one which will form a film or layer on the skin to which it is applied. This localizes the application and provides some resistance to perspiration and/or aids in percutaneous delivery and penetration of the active ingredients into lipid layers. Many such compositions are known in the art, and can take the form of creams, gels, ointments, hydrogels, pastes or plasters, and liquid dosage forms, such as solutions, emulsions, in particular oil-in-water emulsions, suspensions, for example lotions, etc., or even solid sticks. Liposomes or microspheres may also be used.

In some embodiments, the topical formulation will be administered using a device or method designed to more readily break the skin barrier and provide the agents in the topical formulation with a faster or more effective means through the stratum corneum. These include, for example, oxygen nebulizers and nanosomal mist in conjunction with iontophoresis. A spray or nebulizer may be used to create the nanosomel mist. In one embodiment, the micro-electronic cosmetic delivery mechanism described as PowerCosmetics® may be used for delivery of the topical agent to the skin. This method is useful for delivering ionizable compounds to the skin and aids the penetration of small molecules through the stratum corneum. (www.powerpaper.com).

Only effective amounts of each of the components in the topical formulation are needed to treat the signs of aging in skin. Generally, an effective amount of the topical formulation is applied to exposed or affected skin sites in association with a carrier, and particularly one in which the active ingredients are soluble per se or are effectively solubilized (e.g. as an emulsion or microemulsion). The term "an effective amount" of a compound or property means an amount effective in reducing the signs of aging skin, such as wrinkles, pigmentary changes, elastosis, and atrophy. The exact amount required will vary from case to case, depending on recognized variables such as the compounds employed and the individual subject treated. Thus, it is not possible to specify an exact "effective amount" However, an appropriate effective amount may be determined by one of ordinary skill in the art using only routine experimentation.

Preferably, the formulation will contain 0.01 to 80% by weight of the *macqui* berry or *macqui* berry extract. Desirably, it will contain 0.1%-10.0% by weight, or more preferably 1-5% by weight *macqui* berry or *macqui* berry extract. Carriers can be chosen which will solubilize or disperse the active ingredients at such concentrations as provided herein. One particularly efficacious embodiment contains about 1-5% by weight anthocyanins and 1-3% by weight flavonoid glucuronide in a liposomal carrier.

As used herein, the term "treatment of aging skin" means the treatment of the symptoms of skin damage due to either chronoaging or photoaging of the skin, which is characterized by wrinkles, loss of elasticity, and hyper-pigmentation. The treatment is effective to enhance the appearance and/or health of the skin. This includes, for example, reducing oxidative damage in the skin.

The term "effective amount" of a compound or property as provided herein means such an amount as is capable of performing the function of the compound or property for which an effective amount is expressed. As pointed out above, the exact amount required will vary from case to case, depending on recognized variables, such as the compounds employed and the processing conditions observed. Thus, it is not possible to specify an exact "effective amount." However, an appropriate effective amount may be determined by one of ordinary skill in the art using only routine experimentation.

As used herein, the phrase "formulated for use in a beverage" means that the formulation containing the *macqui* berry or *macqui* berry extract is combined with ingredients that are safe for human consumption. Optionally, these ingredients may be to keep the *macqui* berry or *macqui* berry extract in solution or to improve or enhance the flavor or color.

As used herein, the phrase "formulated for use in a candle" means that the formulation containing the *macqui* berry or *macqui* berry extract contains ingredients to keep the formulation stable within candle wax. The formulation may be adapted to keep the formulation mixed within the candle wax to maintain a consistent color, or it may provide optimal release of aromatics from the *macqui* berry or additional source to provide a pleasing smell.

Following long-standing patent law convention, the terms "a" and "an" mean "one or more" when used m this specification Each patent described herein is hereby incorporated by reference in its entirety.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

TABLE 2

| Ingredient | % by weight |
| --- | --- |
| macqui berry extract | 3.0 |
| luteolin 7-glucuronide | 1.0 |
| carriers and excipients | 96.0 |

Example 2

TABLE 3

| Ingredient | % by weight |
| --- | --- |
| macqui berry juice | 5.0 |
| quercetin 3-(isoferulylglucuronide) | 3.0 |
| carriers and excipients | 92.0 |

Example 3

TABLE 4

| Ingredient | % by weight |
| --- | --- |
| macqui berry extract | 3.0 |
| glutathione | 3.0 |
| carnosine | 1.0 |
| carnitine | 1.0 |
| carriers and excipients | 92.0 |

The formulation is encapsulated in a polysaccharide micro-capsule.

Example 4

TABLE 5

| Ingredient | % by weight |
| --- | --- |
| macqui berry extract | 0.5% |
| bilberry extract | 0.5% |
| rosmarinic | 0.1% |
| glutathione | 1.0% |
| green tea polyphenols | 1.0% |
| resveratrol | 0.1% |
| phenyl-butyl-nitrone(PBN) | 0.1% |
| boldine | 0.5% |
| EGF | 0.5% |
| rutin | 0.5% |
| MMP inhibiting glycosaminoglycans | 1.0% |
| tocopherols | 0.5% |
| SOD | 0.5% |
| carriers and excipients | 93.2% |

Example 5

TABLE 6

| Ingredient | % by weight |
| --- | --- |
| macqui berry extract | 1.0% |
| rosmarinic | 0.5% |
| retionol | 1.0% |
| alpha-hydroxy acids | 3.0% |
| allantoin | 2.0% |
| betaine | 5.0% |
| carriers and excipients | 87.5% |

*macqui* berry extract 1.0% Rosmarinic 0.5% Retinal 1.0% Carriers and Excipients 87.5%

Example 6

TABLE 7

| Ingredient | % by weight |
| --- | --- |
| macqui berry extract | 0.1% |
| vigna aconitifolia seed extract | 5% |
| coffe fruit extract | 0.1% |
| saffron extract | 0.01% |
| betacyanins | 0.01% |
| R-lipoic sodium salt | 0.01% |
| rosemary extract | 0.1% |
| ATP | 0.01% |
| EGF | 0.01% |
| carnosine | 0.01% |
| sodium phytate | 0.05% |
| carriers and excipients | 93.2% |

Having described the invention with reference to particular compositions, theories of effectiveness, and the hire, it will be apparent to those skilled in the art that it is not intended that the invention be limited by such illustrative embodiments or mechanisms, and that the modifications can be made without departing from the scope or spirit of the invention, u defined by the appended claims. It is intended that all modifications and variations be included with the scope of the invention. The claims are meant to cover the claimed components and steps in any sequence that is effective to meet the objectives there intended, unless the context specifically indicates the contrary.

The invention claimed is:

1. A topical formulation comprising an effective amount of one or more anthocyanins or a dermatologically acceptable salt thereof, an effective amount of one or more alkaloids, and a stabilizer;
    wherein the one or more anthocyanins are derived from the fruit or leaves of the *Aristotelia Chilensis* plant, or both;
    wherein the one or more alkaloids are derived from the leaves of the *Aristotelia Chilensis* plant;
    and
    wherein the one or more anthocyanins are selected from the group consisting of delphinidins or cyanidins.

2. The formulation of claim 1, wherein the one or more anthocyanins are derived from an extract of maqui berry.

3. The formulation of claim 1, wherein the stabilizer is a glucuronide, a glycuronide, diethylhexyl syringylidene malonate, a microencapsulation agent, or a light and/or air-blocking packaging.

4. The formulation of claim 3, wherein the microencapsulation agent is a liposome or a nano some.

5. The formulation of claim 3, wherein the microencapsulation agent is a biodegradable substance.

6. The formulation of claim 3, wherein the light-blocking packaging blocks light between 450 nm and 750 nm.

7. The formulation claim 1, wherein the one or more anthocyanins are selected from the group consisting of delphinidin-3-glucoarabinoside-5-glucoside; delphinidin 3,5-diglucoside; cyanidin-3-glucoarabinoside-5-glucoside; cyanidin-3,5-diglucoside; delphinidin-3-glucoarabinoside; delphinidin-5-glucoarabinoside; delphinidin-3-glucoside; cyanidin-3-glucoarabinoside; and cyanidin-3-glucoside.

8. The formulation claim 1, further comprising an additional agent.

9. The formulation claim 8, wherein the additional agent is quercetin.

10. The formulation claim 8, wherein the additional agent is an antioxidant.

11. The formulation of claim 10, wherein the additional antioxidant is an antioxidant endogenous to the human body.

12. The formulation claim 10, wherein the additional antioxidant is selected from the group consisting of grape seed procyanidins, tocopherols, tocotrienols, astaxanthin, lutein, lycopene, phytofluene, phytoene, rubixanthin, beta-cryptoxanthin, zeaxanthin, tumeric extract, bilberry anthocyanins, betacyanins, a purified single anthocyanin or combination of selected purified individual anthocyanins, black raspberry extract, blueberry anthocyanins, acai extract, *aronia* extract, prune extract, pomegranate extract, ellagic acid, honokiol, magnolol, silymarin, quercetin, naringenin, rosmarinic acid, rosemary extract, saffron extract, clove essential oil, wolfberry extract, noni fruit extract, *phyllantus emblica* extract, *Camellia sinensis* extract, epicatechin-gallate, *Garcinia mangostana* extract, shikimic acid, montmorency cherry extract, anthocyanin-containing extracts of red, blue, magenta, purple or black flowers, whole coffee fruit extract, chlorogenic acid, caffeic acid, ferulic acid, olive extract, and hydroxytyrosol.

13. The formulation of claim 8, wherein the formulation comprises a metal chelating agent.

14. The formulation claim 1, further comprising an AGE inhibitor, a collagen enhancing agent, a mitochondrial resuscitant, a sunscreen agent, an anti-edemic agent, a glutathione or an inducers thereof, a collagenase-inhibitor, an anti-inflammatory agent, a phenylpropanoid glycoside, a depigmenting agent or agent addressing hyperpigmentation, a skin-protective lipids, hyaluronic acid, an alpha hydroxy acid, an agent useful for treating hormonal decline, an anti-acne agent, an agent altering lipolytic activity, an anti-cellulitic agent, an agent altering anti-capillary-fragility, an anti-elastase agent, an anti-erythema agent, an agent that raises cyclic AMP, or nicotinamide-adenine-dinucleotide.

15. A method of treating skin, said method comprising topically applying an effective amount of the topical formulation of claim 1 to the skin of a subject in need thereof.

16. The method of claim 15, wherein the stabilizer is a glucuronide, a glycuronide, a diethylhexyl syringylidene malonate, microencapsulation agent, or a light and/or air-blocking packaging.

17. The method of claim 16, wherein the microencapsulation agent a liposome or a nanosome.

18. The method of claim 17, wherein the light-blocking packaging blocks light between 450 nm and 750 nm.

* * * * *